(12) United States Patent
Phillips et al.

(10) Patent No.: US 10,537,657 B2
(45) Date of Patent: Jan. 21, 2020

(54) COMPOSITION I-II AND PRODUCTS AND USES THEREOF

(75) Inventors: Marcus Damian Phillips, Hull (GB); Delphine Blanc, Lyons (FR)

(73) Assignees: Smith & Nephew PLC, Watford (GB); Bluestar Silicones France SAS, Lyons (FR)

( * ) Notice: Subject to any disclaimer, the term of this patent is extended or adjusted under 35 U.S.C. 154(b) by 1018 days.

(21) Appl. No.: 13/989,569

(22) PCT Filed: Nov. 25, 2011

(86) PCT No.: PCT/GB2011/001652
§ 371 (c)(1),
(2), (4) Date: Aug. 8, 2013

(87) PCT Pub. No.: WO2012/069794
PCT Pub. Date: May 31, 2012

(65) Prior Publication Data
US 2013/0310781 A1    Nov. 21, 2013

(30) Foreign Application Priority Data

Nov. 25, 2010 (GB) .................................. 1019997.4
Mar. 17, 2011 (GB) .................................. 1104512.7

(51) Int. Cl.
*A61M 1/00* (2006.01)
*A61L 26/00* (2006.01)
(Continued)

(52) U.S. Cl.
CPC ...... *A61L 26/0095* (2013.01); *A61F 13/0216* (2013.01); *A61L 15/26* (2013.01);
(Continued)

(58) Field of Classification Search
CPC ........ A61L 15/425; A61L 15/26; A61L 15/58; A61L 24/0073; A61L 26/0095; A61M 1/00
(Continued)

(56) References Cited

U.S. PATENT DOCUMENTS 3,274,155 A    9/1966 Saunders et al.
3,646,155 A    2/1972 Scott et al.
(Continued)

FOREIGN PATENT DOCUMENTS

CN    1805761      7/2006
CN    101730524    6/2010
(Continued)

OTHER PUBLICATIONS

US 6,216,701 B1, 04/2001, Heaton et al. (withdrawn)
(Continued)

*Primary Examiner* — Andrew J Mensh
(74) *Attorney, Agent, or Firm* — Knobbe, Martens, Olson & Bear, LLP

(57) ABSTRACT

A curable composition apportioned between at least one Part A and at least one Part B, the Parts sealed within barrier means preventing contamination, the at least one Part A comprising: (i) one or more alkenyl-group containing prepolymers having at least one alkenyl group or moiety per molecule, and the at least one Part B comprising: (ii) one or more SiH-containing prepolymers having at least one Si—H unit per molecule; the composition additionally comprising: (iii) a catalyst for curing by addition of alkenyl-containing prepolymer (i) to SiH-containing prepolymer (ii), wherein prepolymer (ii) is substantially absent from Part A and prepolymer (i) is substantially absent from Part B, methods for preparing the composition, methods for sterilisation thereof, medical and non-medical use thereof, a device
(Continued)

incorporating the composition, and a precursor therefor including its sterilisable precursor composition, in particular a terminally sterilisable or terminally sterile composition for medical use, particularly in wound therapy, more particularly as a wound packing material which can be shaped and configured to the shape of a wound, most particularly for application in negative pressure wound therapy (NPWT).

16 Claims, 12 Drawing Sheets

(51) Int. Cl.

| | | |
|---|---|---|
| A61L 15/26 | (2006.01) | |
| A61L 15/42 | (2006.01) | |
| A61L 15/58 | (2006.01) | |
| C08L 83/04 | (2006.01) | |
| A61F 13/02 | (2006.01) | |
| A61L 24/00 | (2006.01) | |
| C08G 77/12 | (2006.01) | |
| C08G 77/20 | (2006.01) | |

(52) U.S. Cl.
CPC .......... *A61L 15/425* (2013.01); *A61L 15/585* (2013.01); *A61L 24/0073* (2013.01); *A61M 1/0088* (2013.01); *C08L 83/04* (2013.01); *C08G 77/12* (2013.01); *C08G 77/20* (2013.01)

(58) Field of Classification Search
USPC .......................................................... 604/319
See application file for complete search history.

(56) References Cited

U.S. PATENT DOCUMENTS

| | | |
|---|---|---|
| 3,783,870 A | 1/1974 | Schachet |
| 3,808,178 A | 4/1974 | Gaylord |
| 3,809,086 A | 5/1974 | Schachet et al. |
| 3,809,087 A | 5/1974 | Lewis, Jr. |
| 3,928,629 A | 12/1975 | Chandra et al. |
| 3,972,328 A | 8/1976 | Chen |
| 4,073,294 A | 2/1978 | Stanley et al. |
| 4,117,551 A | 9/1978 | Books et al. |
| 4,266,545 A | 5/1981 | Moss |
| 4,278,089 A | 7/1981 | Huck et al. |
| 4,392,860 A | 7/1983 | Huck et al. |
| 4,529,553 A | 7/1985 | Faltynek |
| 4,538,920 A | 9/1985 | Drake et al. |
| 4,569,674 A | 2/1986 | Phillips |
| 4,578,060 A | 3/1986 | Huck et al. |
| 4,655,754 A | 4/1987 | Richmond et al. |
| 4,661,093 A | 4/1987 | Beck et al. |
| 4,713,052 A | 12/1987 | Beck et al. |
| 4,714,739 A | 12/1987 | Arkles |
| 4,720,431 A | 1/1988 | Wong |
| 4,728,499 A | 3/1988 | Fehder |
| 4,753,536 A | 6/1988 | Spehar et al. |
| 4,767,026 A | 8/1988 | Keller |
| 4,771,919 A | 9/1988 | Ernst |
| 4,791,149 A * | 12/1988 | Pocknell .............. A61F 13/04 206/221 |
| 4,798,583 A | 1/1989 | Beck et al. |
| 4,813,942 A | 3/1989 | Alvarez |
| 4,826,494 A | 5/1989 | Richmond et al. |
| 4,872,450 A | 10/1989 | Austad |
| 4,923,444 A | 5/1990 | Daoud et al. |
| 4,936,834 A | 6/1990 | Beck et al. |
| 4,969,880 A | 11/1990 | Zamierowski |
| 4,991,574 A | 2/1991 | Pocknell |
| 5,004,643 A * | 4/1991 | Caldwell ........... A61F 13/00008 427/358 |
| 5,010,115 A | 4/1991 | Grisoni |
| 5,033,650 A | 7/1991 | Colin et al. |
| 5,056,510 A | 10/1991 | Gilman |
| 5,064,653 A | 11/1991 | Sessions et al. |
| 5,080,493 A | 1/1992 | McKown et al. |
| 5,089,606 A | 2/1992 | Cole et al. |
| 5,100,395 A | 3/1992 | Rosenberg |
| 5,141,503 A | 8/1992 | Sewell, Jr. |
| 5,145,933 A | 9/1992 | Grisoni et al. |
| 5,153,231 A * | 10/1992 | Bouquet .............. A61C 9/0026 424/447 |
| 5,181,905 A | 1/1993 | Flam |
| 5,238,732 A | 8/1993 | Krishnan |
| 5,249,709 A | 10/1993 | Duckworth et al. |
| 5,266,326 A | 11/1993 | Barry et al. |
| 5,333,760 A | 8/1994 | Simmen et al. |
| 5,348,392 A | 9/1994 | Bouquet et al. |
| 5,397,848 A | 3/1995 | Yang et al. |
| 5,456,745 A | 10/1995 | Rorefer et al. |
| 5,549,584 A | 8/1996 | Gross |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,636,643 A | 6/1997 | Argenta et al. |
| 5,645,081 A | 7/1997 | Argenta et al. |
| 5,660,823 A | 8/1997 | Chakrabarti et al. |
| 5,717,030 A | 2/1998 | Dunn et al. |
| 5,747,064 A | 5/1998 | Burnett et al. |
| 5,759,570 A | 6/1998 | Arnold |
| 5,776,193 A | 7/1998 | Kwan et al. |
| 5,834,007 A | 11/1998 | Kubota |
| 5,840,777 A | 11/1998 | Eagles et al. |
| 5,852,126 A | 12/1998 | Barnard et al. |
| 5,874,500 A | 2/1999 | Rhee et al. |
| D406,899 S | 3/1999 | Cottle |
| RE36,235 E | 6/1999 | Keller et al. |
| 5,944,703 A | 8/1999 | Dixon et al. |
| 5,945,115 A | 8/1999 | Dunn et al. |
| 5,962,010 A | 10/1999 | Greff et al. |
| 5,998,472 A | 12/1999 | Berger et al. |
| 6,024,731 A | 2/2000 | Seddon et al. |
| 6,065,270 A | 5/2000 | Reinhard et al. |
| 6,071,267 A | 6/2000 | Zamierowski |
| 6,135,116 A | 10/2000 | Vogel et al. |
| D434,150 S | 11/2000 | Tumey et al. |
| 6,142,982 A | 11/2000 | Hunt et al. |
| 6,143,352 A | 11/2000 | Clark et al. |
| 6,165,201 A | 12/2000 | Sawhney et al. |
| 6,168,788 B1 | 1/2001 | Wortham |
| D439,341 S | 3/2001 | Tumey et al. |
| 6,214,332 B1 | 4/2001 | Askill et al. |
| 6,252,129 B1 | 6/2001 | Coffee |
| 6,261,276 B1 | 7/2001 | Reitsma |
| 6,345,623 B1 | 2/2002 | Heaton et al. |
| 6,391,294 B1 | 5/2002 | Dettmar et al. |
| 6,398,761 B1 | 6/2002 | Bills et al. |
| 6,447,802 B2 | 9/2002 | Sessions et al. |
| 6,458,109 B1 | 10/2002 | Henley et al. |
| 6,486,285 B2 | 11/2002 | Fujita |
| 6,495,127 B1 | 12/2002 | Wallace et al. |
| 6,509,031 B1 | 1/2003 | Miller et al. |
| 6,521,251 B2 | 2/2003 | Askill et al. |
| 6,527,203 B2 | 3/2003 | Hurray et al. |
| 6,547,467 B2 * | 4/2003 | Quintero .......... A61B 17/00491 206/438 |
| 6,553,998 B2 | 4/2003 | Heaton et al. |
| 6,564,972 B2 | 5/2003 | Sawhney et al. |
| 6,569,113 B2 | 5/2003 | Wirt et al. |
| 6,575,940 B1 | 6/2003 | Levinson et al. |
| 6,596,704 B1 | 7/2003 | Court et al. |
| 6,626,891 B2 | 9/2003 | Ohmstede |
| 6,627,216 B2 | 9/2003 | Brandt et al. |
| 6,629,774 B1 | 10/2003 | Gruendeman |
| 6,648,852 B2 | 11/2003 | Wirt et al. |
| 6,648,862 B2 | 11/2003 | Watson |
| 6,685,681 B2 | 2/2004 | Lockwood et al. |
| 6,695,823 B1 | 2/2004 | Lina et al. |
| 6,698,622 B2 | 3/2004 | Sawhney et al. |
| 6,730,299 B1 | 5/2004 | Tayot et al. |
| 6,732,887 B2 | 5/2004 | Bills |

(56) References Cited

U.S. PATENT DOCUMENTS

| | | |
|---|---|---|
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,776,769 B2 | 8/2004 | Smith |
| 6,790,438 B1 | 9/2004 | Constancis et al. |
| 6,800,074 B2 | 10/2004 | Henley et al. |
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,840,462 B2 | 1/2005 | Hurray et al. |
| 6,855,135 B2 | 2/2005 | Lockwood et al. |
| 6,856,821 B2 | 2/2005 | Johnson |
| 6,926,695 B2 | 8/2005 | Levinson et al. |
| 6,936,037 B2 | 8/2005 | Bubb |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,128,735 B2 | 10/2006 | Weston |
| 7,129,210 B2 | 10/2006 | Lowinger et al. |
| 7,132,170 B2 | 11/2006 | Parker |
| 7,175,336 B2 | 2/2007 | Voellmicke et al. |
| 7,216,651 B2 | 5/2007 | Argenta et al. |
| 7,279,612 B1 | 10/2007 | Heaton et al. |
| 7,303,757 B2 | 12/2007 | Schankereli et al. |
| 7,316,330 B2 | 1/2008 | Muller et al. |
| 7,361,184 B2 | 4/2008 | Joshi |
| 7,381,859 B2 | 6/2008 | Hunt et al. |
| 7,387,432 B2 | 6/2008 | Lu et al. |
| 7,396,507 B2 | 7/2008 | Grunwald et al. |
| 7,524,315 B2 | 4/2009 | Blott et al. |
| 7,534,927 B2 | 5/2009 | Lockwood |
| 7,543,843 B2 | 6/2009 | Keshavaraj et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,635,343 B2 | 12/2009 | McIntosh et al. |
| 7,674,837 B2 | 3/2010 | Gaserod et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,708,940 B2 | 5/2010 | Grunwald et al. |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,723,560 B2 | 5/2010 | Lockwood et al. |
| 7,749,531 B2 | 7/2010 | Booher |
| 7,758,554 B2 | 7/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,862,831 B2 | 1/2011 | Wang et al. |
| 7,882,983 B2 | 2/2011 | Reidt et al. |
| 7,910,135 B2 | 3/2011 | St. John et al. |
| 7,910,791 B2 | 3/2011 | Coffey |
| 7,919,182 B2 | 4/2011 | Hamada et al. |
| 7,922,703 B2 | 4/2011 | Riesinger |
| 7,922,743 B2 | 4/2011 | Heinrich et al. |
| 7,927,318 B2 | 4/2011 | Risk, Jr. et al. |
| 7,959,624 B2 | 6/2011 | Riesinger |
| 7,964,766 B2 | 6/2011 | Blott et al. |
| 7,954,672 B2 | 7/2011 | Keller |
| 7,976,519 B2 | 7/2011 | Bubb et al. |
| 8,007,164 B2 | 8/2011 | Tatsunosuke et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,331 B2 | 11/2011 | Zamierowski |
| 8,074,843 B2 | 12/2011 | Keller |
| 8,080,702 B2 | 12/2011 | Blott et al. |
| 8,096,979 B2 | 1/2012 | Lina et al. |
| 8,100,887 B2 | 1/2012 | Weston et al. |
| 8,118,794 B2 | 2/2012 | Weston et al. |
| 8,119,160 B2 | 2/2012 | Looney et al. |
| 8,162,907 B2 | 4/2012 | Heagle |
| 8,162,909 B2 | 4/2012 | Blott et al. |
| 8,168,848 B2 | 5/2012 | Lockwood et al. |
| 8,192,409 B2 | 6/2012 | Hardman et al. |
| 8,207,392 B2 | 6/2012 | Haggstrom et al. |
| 8,225,981 B2 | 7/2012 | Criscuolo et al. |
| 8,226,942 B2 | 7/2012 | Charier et al. |
| 8,235,972 B2 | 8/2012 | Adahan |
| 8,241,261 B2 | 8/2012 | Randolph et al. |
| 8,267,918 B2 | 9/2012 | Johnson et al. |
| 8,273,368 B2 | 9/2012 | Ambrosio et al. |
| 8,282,611 B2 | 10/2012 | Weston |
| 8,286,832 B2 | 10/2012 | Keller |
| 8,303,552 B2 | 11/2012 | Weston |
| 8,372,049 B2 | 2/2013 | Jaeb et al. |
| 8,372,050 B2 | 2/2013 | Jaeb et al. |
| 8,382,731 B2 | 2/2013 | Johannison |
| 8,410,189 B2 | 4/2013 | Carnahan et al. |
| 8,425,478 B2 | 4/2013 | Olson |
| 8,444,612 B2 | 5/2013 | Patel et al. |
| 8,454,580 B2 | 6/2013 | Locke et al. |
| 8,460,255 B2 | 6/2013 | Joshi et al. |
| 8,481,801 B2 | 7/2013 | Addison et al. |
| 8,535,296 B2 | 9/2013 | Blott et al. |
| 8,540,699 B2 | 9/2013 | Miller et al. |
| 8,613,734 B2 | 12/2013 | Lina et al. |
| 8,628,505 B2 | 1/2014 | Weston |
| 8,641,691 B2 | 2/2014 | Fink |
| 8,663,198 B2 | 3/2014 | Buan et al. |
| 8,708,998 B2 | 4/2014 | Weston et al. |
| 8,715,256 B2 | 5/2014 | Greener |
| 8,753,670 B2 | 6/2014 | Delmotte |
| 8,764,732 B2 | 7/2014 | Hartwell |
| 8,791,316 B2 | 7/2014 | Greener |
| 8,795,243 B2 | 8/2014 | Weston |
| 8,795,635 B2 | 8/2014 | Tamarkin et al. |
| 8,795,713 B2 | 8/2014 | Makower et al. |
| 8,795,800 B2 | 8/2014 | Evans |
| 8,801,685 B2 | 8/2014 | Armstrong et al. |
| 8,808,274 B2 | 8/2014 | Hartwell |
| 8,834,451 B2 | 9/2014 | Blott et al. |
| 8,843,327 B2 | 9/2014 | Vernon-Harcourt et al. |
| 8,894,620 B2 | 11/2014 | Swain |
| 8,916,742 B2 | 12/2014 | Smith |
| 8,968,773 B2 | 3/2015 | Thomas et al. |
| 8,998,866 B2 | 4/2015 | Hicks |
| 9,028,872 B2 | 5/2015 | Gaserod et al. |
| 9,061,095 B2 | 6/2015 | Adie et al. |
| 9,067,003 B2 | 6/2015 | Buan et al. |
| 9,173,777 B2 | 11/2015 | Zurovcik |
| 9,220,822 B2 | 12/2015 | Hartwell et al. |
| 9,387,126 B2 | 7/2016 | Blott et al. |
| 9,682,179 B2 | 6/2017 | May |
| 2001/0004082 A1 | 6/2001 | Keller et al. |
| 2001/0043913 A1 | 11/2001 | Spaans et al. |
| 2002/0010299 A1 | 1/2002 | Guyuron et al. |
| 2002/0038826 A1 | 4/2002 | Hurray et al. |
| 2002/0122771 A1 | 9/2002 | Holland et al. |
| 2002/0143286 A1 | 10/2002 | Tumey |
| 2002/0145007 A1 | 10/2002 | Sawhney et al. |
| 2002/0146662 A1 | 10/2002 | Radl et al. |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2003/0040478 A1 | 2/2003 | Drucker et al. |
| 2003/0069535 A1 | 4/2003 | Shalaby |
| 2003/0069563 A1 | 4/2003 | Johnson |

(56) References Cited

U.S. PATENT DOCUMENTS

| | | |
|---|---|---|
| 2003/0093041 A1 | 5/2003 | Risk, Jr. et al. |
| 2003/0125646 A1 | 7/2003 | Whitlock |
| 2003/0143189 A1 | 7/2003 | Askill et al. |
| 2003/0183653 A1 | 10/2003 | Bills |
| 2003/0212357 A1 | 11/2003 | Pace |
| 2004/0006319 A1 | 1/2004 | Lina et al. |
| 2004/0033466 A1 | 2/2004 | Shellard et al. |
| 2004/0037897 A1 | 2/2004 | Benjamin et al. |
| 2004/0049187 A1 | 3/2004 | Burnett et al. |
| 2004/0057855 A1 | 3/2004 | Gerlach et al. |
| 2004/0073152 A1 | 4/2004 | Karason et al. |
| 2004/0084812 A1 | 5/2004 | Grunwald et al. |
| 2004/0121438 A1 | 6/2004 | Quirk |
| 2004/0167617 A1 | 8/2004 | Voellmicke et al. |
| 2004/0171998 A1 | 9/2004 | Marasco, Jr. |
| 2005/0020955 A1 | 1/2005 | Sanders et al. |
| 2005/0085795 A1 | 4/2005 | Lockwood |
| 2005/0100692 A1 | 5/2005 | Parker |
| 2005/0137272 A1 | 6/2005 | Gaserod et al. |
| 2005/0163904 A1 | 7/2005 | Walker et al. |
| 2005/0230422 A1 | 10/2005 | Muller et al. |
| 2006/0009577 A1 | 1/2006 | Hara |
| 2006/0009744 A1 | 1/2006 | Edrman et al. |
| 2006/0079599 A1 | 4/2006 | Arthur |
| 2006/0100586 A1 | 5/2006 | Karpowicz |
| 2006/0173253 A1 | 8/2006 | Ganapathy et al. |
| 2006/0173514 A1 | 8/2006 | Biel et al. |
| 2006/0217016 A1 | 9/2006 | Lin et al. |
| 2006/0228318 A1 | 10/2006 | Fabo |
| 2006/0253082 A1 | 11/2006 | McIntosh et al. |
| 2006/0273109 A1 | 12/2006 | Keller |
| 2007/0004896 A1 | 1/2007 | Ito et al. |
| 2007/0009580 A1 | 1/2007 | DiCosmo et al. |
| 2007/0040454 A1 | 2/2007 | Freudenberger et al. |
| 2007/0055209 A1 | 3/2007 | Patel et al. |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0185426 A1 | 8/2007 | Abrosio et al. |
| 2007/0185463 A1 | 8/2007 | Mulligan |
| 2007/0186404 A1 | 8/2007 | Drew et al. |
| 2007/0203062 A1 | 8/2007 | Ellis-Behnke et al. |
| 2007/0219513 A1 | 9/2007 | Lina et al. |
| 2007/0225663 A1 | 9/2007 | Watt et al. |
| 2007/0237811 A1 | 10/2007 | Scherr |
| 2007/0248642 A1 | 10/2007 | Dornish et al. |
| 2008/0004549 A1 | 1/2008 | Anderson et al. |
| 2008/0031748 A1 | 2/2008 | Ihle et al. |
| 2008/0060550 A1 | 3/2008 | MacDonald et al. |
| 2008/0089173 A1 | 4/2008 | Lu et al. |
| 2008/0132821 A1 | 6/2008 | Propp et al. |
| 2008/0206155 A1 | 8/2008 | Tamarkin et al. |
| 2008/0208163 A1 | 8/2008 | Wilkie |
| 2008/0232187 A1 | 9/2008 | Tatsunosuke et al. |
| 2008/0249259 A1* | 10/2008 | Kashiwagi ............... C08L 83/04 525/478 |
| 2008/0254103 A1 | 10/2008 | Harris et al. |
| 2008/0279807 A1 | 11/2008 | Belcheva et al. |
| 2008/0287880 A1 | 11/2008 | Keller |
| 2008/0306456 A1 | 12/2008 | Riesinger |
| 2008/0314929 A1 | 12/2008 | Keller |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0093550 A1 | 4/2009 | Rolfes et al. |
| 2009/0098073 A1 | 4/2009 | MacDonald et al. |
| 2009/0098503 A1 | 4/2009 | Knispel et al. |
| 2009/0134186 A1 | 5/2009 | Keller |
| 2009/0157017 A1 | 6/2009 | Ambrosio |
| 2009/0196844 A1 | 8/2009 | Choi et al. |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0254053 A1 | 10/2009 | Svensby et al. |
| 2009/0275872 A1 | 11/2009 | Addison et al. |
| 2009/0299251 A1 | 12/2009 | Buan |
| 2009/0299255 A1 | 12/2009 | Kazala, Jr. et al. |
| 2009/0299306 A1 | 12/2009 | Buan |
| 2010/0012210 A1 | 1/2010 | Miyano et al. |
| 2010/0022972 A1 | 1/2010 | Lina et al. |
| 2010/0030132 A1 | 2/2010 | Niezgoda et al. |
| 2010/0036305 A1 | 2/2010 | Green |
| 2010/0036334 A1 | 2/2010 | Heagle et al. |
| 2010/0069850 A1 | 3/2010 | Fabo |
| 2010/0125258 A1 | 5/2010 | Coulthard et al. |
| 2010/0125259 A1 | 5/2010 | Olson |
| 2010/0135915 A1 | 6/2010 | Greener |
| 2010/0137775 A1 | 6/2010 | Hu et al. |
| 2010/0230467 A1 | 9/2010 | Crisuolo et al. |
| 2010/0259406 A1 | 10/2010 | Caso et al. |
| 2010/0268177 A1 | 10/2010 | Hall |
| 2010/0305526 A1 | 12/2010 | Robinson et al. |
| 2010/0318052 A1 | 12/2010 | Ha et al. |
| 2010/0324510 A1 | 12/2010 | Andresen et al. |
| 2011/0004172 A1 | 1/2011 | Eckstein et al. |
| 2011/0021431 A1 | 1/2011 | Jones et al. |
| 2011/0028919 A1 | 2/2011 | Johnnison et al. |
| 2011/0033503 A1 | 2/2011 | Sinko et al. |
| 2011/0036889 A1 | 2/2011 | Heinrich et al. |
| 2011/0066123 A1 | 3/2011 | Tout et al. |
| 2011/0086077 A1 | 4/2011 | McCrea et al. |
| 2011/0118683 A1 | 5/2011 | Weston |
| 2011/0144599 A1 | 6/2011 | Croizat et al. |
| 2011/0147432 A1 | 6/2011 | Heinrich et al. |
| 2011/0147435 A1 | 6/2011 | Heinrich et al. |
| 2011/0224631 A1 | 9/2011 | Simmons |
| 2011/0250447 A1* | 10/2011 | Taniguchi ............... A61L 15/58 428/355 R |
| 2011/0257611 A1 | 10/2011 | Locke et al. |
| 2011/0313374 A1 | 12/2011 | Lockwood et al. |
| 2011/0319804 A1 | 12/2011 | Greener |
| 2012/0041399 A1 | 2/2012 | Blott et al. |
| 2012/0051945 A1 | 3/2012 | Orndorff et al. |
| 2012/0083755 A1 | 4/2012 | Lina et al. |
| 2012/0095380 A1 | 4/2012 | Gergley et al. |
| 2012/0116334 A1 | 5/2012 | Albert et al. |
| 2012/0123356 A1 | 5/2012 | Greener |
| 2012/0123358 A1 | 5/2012 | Hall et al. |
| 2012/0222687 A1 | 9/2012 | Czajka, Jr. et al. |
| 2013/0023841 A1 | 1/2013 | Johnson et al. |
| 2013/0090616 A1 | 4/2013 | Neubauer |
| 2013/0096519 A1 | 4/2013 | Blott |
| 2013/0116635 A1 | 5/2013 | Fleischmann |
| 2013/0116641 A1 | 5/2013 | Hicks |
| 2013/0138054 A1 | 5/2013 | Fleischmann |
| 2013/0138060 A1 | 5/2013 | Haqqstrom et al. |
| 2013/0144227 A1 | 6/2013 | Locke et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0245583 A1 | 9/2013 | Locke et al. |
| 2013/0274688 A1 | 10/2013 | Weston |
| 2013/0296762 A1 | 11/2013 | Toth |
| 2013/0302545 A1 | 11/2013 | Schnelker et al. |
| 2013/0310780 A1 | 11/2013 | Phillips |
| 2013/0331822 A1 | 12/2013 | Patel et al. |
| 2013/0338613 A1 | 12/2013 | Haggstrom et al. |
| 2014/0012214 A1 | 1/2014 | Miller et al. |
| 2014/0114268 A1 | 4/2014 | Auguste et al. |
| 2014/0171888 A1 | 6/2014 | Croizat et al. |
| 2014/0228791 A1 | 8/2014 | Hartwell |
| 2014/0228792 A1 | 8/2014 | Hartwell |
| 2014/0249493 A1 | 9/2014 | Hartwell |
| 2014/0316359 A1 | 10/2014 | Collinson et al. |
| 2015/0159066 A1 | 6/2015 | Hartwell et al. |
| 2015/0190286 A1 | 7/2015 | Allen et al. |
| 2015/0216733 A1 | 8/2015 | Allen et al. |

(56) References Cited

U.S. PATENT DOCUMENTS

| | | | |
|---|---|---|---|
| 2016/0120706 A1 | 5/2016 | Collinson et al. | |
| 2016/0144084 A1 | 5/2016 | Collinson et al. | |

FOREIGN PATENT DOCUMENTS

| | | |
|---|---|---|
| DE | 34 43 101 | 5/1986 |
| DE | 3 838 587 | 5/1990 |
| DE | 20 2004 017 0 | 7/2005 |
| EP | 0251810 A2 | 1/1988 |
| EP | 0 358 302 | 3/1990 |
| EP | 0 425 164 | 5/1991 |
| EP | 0425164 A1 | 5/1991 |
| EP | 0 322 118 | 6/1992 |
| EP | 0 521 434 | 7/1993 |
| EP | 0 325 771 | 9/1993 |
| EP | 0 617 152 | 9/1994 |
| EP | 0 578 999 | 5/1996 |
| EP | 0 549 781 | 9/1996 |
| EP | 0 762 860 | 3/1997 |
| EP | 0 506 241 | 5/1997 |
| EP | 0 793 019 | 9/1997 |
| EP | 0 620 720 | 3/1998 |
| EP | 0 858 810 | 8/1998 |
| EP | 0 651 983 | 9/1998 |
| EP | 0 888 141 | 1/1999 |
| EP | 0 912 251 | 5/1999 |
| EP | 0 923 905 | 6/1999 |
| EP | 1 007 015 | 6/2000 |
| EP | 1 013 290 | 6/2000 |
| EP | 1 029 585 | 8/2000 |
| EP | 1 030 657 | 8/2000 |
| EP | 0 688 189 | 9/2000 |
| EP | 1 088 569 | 4/2001 |
| EP | 1 105 171 | 6/2001 |
| EP | 1 105 180 | 6/2001 |
| EP | 1 107 813 | 6/2001 |
| EP | 1 114 933 | 7/2001 |
| EP | 1 139 951 | 10/2001 |
| EP | 0 921 775 | 12/2001 |
| EP | 1 177 781 | 2/2002 |
| EP | 1 219 311 | 7/2002 |
| EP | 1 283 702 | 2/2003 |
| EP | 1 306 123 | 2/2003 |
| EP | 1 374 914 | 1/2004 |
| EP | 1 374 915 | 1/2004 |
| EP | 1 440 737 | 7/2004 |
| EP | 1 018 967 | 8/2004 |
| EP | 1 476 217 | 11/2004 |
| EP | 1633830 A2 | 1/2005 |
| EP | 1 637 088 | 3/2006 |
| EP | 1 171 065 | 3/2007 |
| EP | 1 798 835 | 6/2007 |
| EP | 1 955 887 | 8/2008 |
| EP | 1 978 046 | 10/2008 |
| EP | 1978046 | 10/2008 |
| EP | 1 993 512 A2 | 11/2008 |
| EP | 1988125 A2 | 11/2008 |
| EP | 2 010 065 | 1/2009 |
| EP | 2 111 804 | 10/2009 |
| EP | 2 127 690 | 12/2009 |
| EP | 2 263 627 | 12/2010 |
| EP | 1 374 914 B1 | 3/2011 |
| EP | 2335747 A1 | 6/2011 |
| EP | 2 366 721 | 9/2011 |
| EP | 2366721 | 9/2011 |
| EP | 2 462 908 | 6/2012 |
| EP | 2 529 767 | 12/2012 |
| EP | 2 477 674 | 7/2013 |
| EP | 2 643 027 A1 | 10/2013 |
| EP | 2 643 412 | 10/2013 |
| EP | 2 451 498 | 4/2014 |
| EP | 2 544 642 | 1/2015 |
| EP | 2 648 668 | 1/2015 |
| EP | 2 830 555 | 2/2015 |
| FR | 1163907 | 10/1958 |
| GB | 2288734 | 11/1995 |
| GB | 2306580 | 5/1997 |
| GB | 2329127 | 3/1999 |
| GB | 2305610 | 7/1999 |
| GB | 2389794 | 12/2003 |
| GB | 2423019 | 8/2006 |
| GB | 2424582 | 10/2006 |
| GB | 2435419 | 2/2007 |
| GB | 2 435 422 | 8/2007 |
| JP | S59-36608 | 2/1984 |
| JP | H05-070692 | 3/1993 |
| JP | 2005 261376 | 9/2005 |
| JP | 2005-334188 | 12/2005 |
| JP | 2009-148393 | 7/2009 |
| JP | 2009-542408 | 12/2009 |
| WO | WO 1992/009301 | 6/1992 |
| WO | WO 1992/09651 | 6/1992 |
| WO | WO 1992/10983 | 7/1992 |
| WO | WO 1993/06802 | 4/1993 |
| WO | WO 1993/09176 | 5/1993 |
| WO | WO 1993/09727 | 5/1993 |
| WO | WO 1994/020133 | 9/1994 |
| WO | WO 1994/21207 | 9/1994 |
| WO | WO 1995/04511 | 2/1995 |
| WO | WO 1995/029959 | 11/1995 |
| WO | WO 1996/01731 | 1/1996 |
| WO | WO 1996/05873 | 2/1996 |
| WO | WO 1996/40174 | 12/1996 |
| WO | WO 1997/03717 | 2/1997 |
| WO | WO 1997/11658 | 4/1997 |
| WO | WO 1997/14384 | 4/1997 |
| WO | WO 1997/33922 | 9/1997 |
| WO | WO 1997/38732 | 10/1997 |
| WO | WO 1997/42986 | 11/1997 |
| WO | WO 1997/43991 | 11/1997 |
| WO | WO 1998/03267 | 1/1998 |
| WO | WO 1998/06444 | 2/1998 |
| WO | WO 1998/13000 | 4/1998 |
| WO | WO 1999/17698 | 4/1999 |
| WO | WO 1999/19013 | 4/1999 |
| WO | WO 1999/30629 | 6/1999 |
| WO | WO 1999/39671 | 8/1999 |
| WO | WO 1999/047097 | 9/1999 |
| WO | WO 1999/48621 | 9/1999 |
| WO | WO 1999/65536 | 12/1999 |
| WO | WO 2000/00016 | 1/2000 |
| WO | WO 2000/17968 | 3/2000 |
| WO | WO 2000/38752 | 7/2000 |
| WO | WO 2000/40190 | 7/2000 |
| WO | WO 2000/61206 | 10/2000 |
| WO | WO 2000/62827 | 10/2000 |
| WO | WO 2000/064396 | 11/2000 |
| WO | WO 2000/074738 | 12/2000 |
| WO | WO 2001/10363 | 2/2001 |
| WO | WO 2001/37773 | 5/2001 |
| WO | WO 2001/49233 | 7/2001 |
| WO | WO 2001/062312 | 8/2001 |
| WO | WO 2001/066017 | 9/2001 |
| WO | WO 2001/072251 | 10/2001 |
| WO | WO 2001/87271 | 11/2001 |
| WO | WO 2001/89588 | 11/2001 |
| WO | WO 2002/02079 | 1/2002 |
| WO | WO 2002/05737 | 1/2002 |
| WO | WO 2002/17840 | 3/2002 |
| WO | WO 2002/24132 | 3/2002 |
| WO | WO 2002/38096 | 5/2002 |
| WO | WO 2002/070040 | 9/2002 |
| WO | WO 2002/094256 | 11/2002 |
| WO | WO 2002/102864 | 12/2002 |
| WO | WO 2003/005943 | 1/2003 |
| WO | WO 2003/022333 | 3/2003 |
| WO | WO 2003/041786 | 5/2003 |
| WO | WO 2003/065877 | 8/2003 |
| WO | WO 2003/072748 | 9/2003 |
| WO | WO 2004/016313 | 2/2004 |
| WO | WO 2004/037334 | 5/2004 |
| WO | WO 2004/052982 | 6/2004 |
| WO | WO 2004/054632 | 7/2004 |
| WO | WO 2004/060148 | 7/2004 |

(56) References Cited

FOREIGN PATENT DOCUMENTS

| | | |
|---|---|---|
| WO | WO 2004/077387 | 9/2004 |
| WO | WO 2004/098474 | 11/2004 |
| WO | WO 2004/108175 | 12/2004 |
| WO | WO 2005/009488 | 2/2005 |
| WO | WO 2005/017000 | 2/2005 |
| WO | WO 2005/018695 | 3/2005 |
| WO | WO 2005/019343 | 3/2005 |
| WO | WO 2005/025447 | 3/2005 |
| WO | WO 2005/046760 | 5/2005 |
| WO | WO 2005/082435 | 9/2005 |
| WO | WO 2005/118011 | 12/2005 |
| WO | WO 2005/123170 | 12/2005 |
| WO | WO 2006/005939 | 1/2006 |
| WO | WO 2006/014534 | 2/2006 |
| WO | WO 2006/028244 | 3/2006 |
| WO | WO 2006/030054 | 3/2006 |
| WO | WO 2006/034128 | 3/2006 |
| WO | WO 2006/034166 | 3/2006 |
| WO | WO 2006/046060 | 5/2006 |
| WO | WO 2006/052839 | 5/2006 |
| WO | WO 2006/081403 | 8/2006 |
| WO | WO 2006/114637 | 11/2006 |
| WO | WO 2006/116992 | 11/2006 |
| WO | WO 2006/135506 | 12/2006 |
| WO | WO 2006/135934 | 12/2006 |
| WO | WO 2007/031757 | 3/2007 |
| WO | WO 2007/031762 | 3/2007 |
| WO | WO 2007/092397 | 8/2007 |
| WO | WO 2007/095180 | 8/2007 |
| WO | WO 2007/106590 | 9/2007 |
| WO | WO 2007/106594 | 9/2007 |
| WO | WO 2007/116347 | 10/2007 |
| WO | WO 2007/123451 | 11/2007 |
| WO | WO 2007/124198 | 11/2007 |
| WO | WO 2007/133618 | 11/2007 |
| WO | WO 2007/143060 | 12/2007 |
| WO | WO 2008/008032 | 1/2008 |
| WO | WO 2008/028494 | 3/2008 |
| WO | WO 2008/036162 | 3/2008 |
| WO | WO 2008/039223 | 4/2008 |
| WO | WO 2008/040681 | 4/2008 |
| WO | WO 2008/043067 | 4/2008 |
| WO | WO 2008/060475 | 5/2008 |
| WO | WO 2008/076407 | 6/2008 |
| WO | WO 2008/082444 | 7/2008 |
| WO | WO 2008/086397 | 7/2008 |
| WO | WO 2008/100437 | 8/2008 |
| WO | WO 2008/104609 | 9/2008 |
| WO | WO 2008/134544 | 11/2008 |
| WO | WO 2008/134774 | 11/2008 |
| WO | WO 2008/135997 | 11/2008 |
| WO | WO 2009/011856 | 1/2009 |
| WO | WO 2009/042514 | 4/2009 |
| WO | WO 2009/047524 | 4/2009 |
| WO | WO 2009/052193 | 4/2009 |
| WO | WO 2009/060327 | 5/2009 |
| WO | WO 2009/062327 | 5/2009 |
| WO | WO 2009/077722 | 6/2009 |
| WO | WO 2009/086580 | 7/2009 |
| WO | WO 2009/088925 | 7/2009 |
| WO | WO 2009/090074 | 7/2009 |
| WO | WO 2009/102021 | 8/2009 |
| WO | WO 2009/103031 | 8/2009 |
| WO | WO 2009/122989 | 10/2009 |
| WO | WO 2009/124100 | 10/2009 |
| WO | WO 2009/124407 | 10/2009 |
| WO | WO 2009/126102 A1 | 10/2009 |
| WO | WO 2009/146441 | 12/2009 |
| WO | WO 2009/156709 | 12/2009 |
| WO | WO 2009/158128 | 12/2009 |
| WO | WO 2010/006182 | 1/2010 |
| WO | WO 2010/19997 | 1/2010 |
| WO | WO 2010/121033 | 10/2010 |
| WO | WO 2010/122665 | 10/2010 |
| WO | WO 2010/142959 | 12/2010 |
| WO | WO 2010/147533 | 12/2010 |
| WO | WO 2011/072840 | 6/2011 |
| WO | WO 2011/112870 | 9/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/009370 | 1/2012 |
| WO | WO 2012/041296 | 4/2012 |
| WO | WO 2012/069793 | 5/2012 |
| WO | WO 2012/069793 A1 | 5/2012 |
| WO | WO 2012/069794 | 5/2012 |
| WO | WO 2012/074512 | 6/2012 |
| WO | WO 2012/078707 | 6/2012 |
| WO | WO 2012/131237 | 10/2012 |
| WO | WO 2012/140378 | 10/2012 |
| WO | WO 2012/143665 | 10/2012 |
| WO | WO 2013/010907 | 1/2013 |
| WO | WO 2013/029652 | 3/2013 |
| WO | WO 2013/033131 | 3/2013 |
| WO | WO 2013/064852 | 5/2013 |
| WO | WO 2013/076450 | 5/2013 |
| WO | WO 2013/083800 | 6/2013 |
| WO | WO 2013/110008 | 7/2013 |
| WO | WO 2013/149078 | 10/2013 |
| WO | WO 2013/136181 | 11/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2015/022334 | 2/2015 |

OTHER PUBLICATIONS

Letter/Observations from Dr. Tanja Bendele, LL.M. at RUHR re EP 2643027, dated May 29, 2015 in 10 pages.
U.S. Appl. No. 14/254,633, filed Apr. 16, 2014, Weston et al.
Jahns et al., Poster "Problemwundversorgung mit einem neuen anschmiegsamen Silikonschaumverband mit Anwendung der Vakuumtechnik," 2nd Congress of German Wound Treatment Society 1998.
Khan, et al., "Influence of Chitosan Molecular Weight on its Physical Properties", EIMJM (2003); 2(1); pp. 1-8.
Letter from Dr. Tanja Bendele, LL.M at RUHRre EP 2643412 dated May 21, 2014 in 9 pages.
Letter/Opposition from Dr. Tanja Bendele, LL.M at RUHR re EP 2643027, dated May 21, 2014 in 17 pages.
Sogias, et al., "Exploring the Factors Affecting the Solubility of Chitosan in Water", Macromol. Chem. Phys. (2010); 211; pp. 426-433.
Wooding-Scott, Margaret, et al., "No Wound is Too Big for Resourceful Nurses," RN Dec. 1988, pp. 22-25 USA.
European Observations by third Party, re EPO App. No. 11 811 106.1, dated Apr. 9, 2015.
He Sihuang, Beijeing: Quality Management in Drug Production, China Medical Science Press, p. 65-66, Feb. 28, 2009).
Letter/Objections from Dr. Tanja Bendele, LL.M. at RUHR re EP 2643412 dated Apr. 1, 2015 in 10 pages.
International Search Report dated Mar. 6, 2012 in International Application No. PCT/GB2011/001649 in 4 pages.
International Search Report dated May 18, 2012 in International Application No. PCT/GB2011/001652 in 6 pages.
X-ray Sterlisation: The Technology of the Future dated Feb. 1, 2010. Retrieved from http://www.emdt.co.uk/article/x-ray-sterilisation-technology-future.
X-ray Sterlisation dated Mar. 1, 2008. Retrieved from http://www.emdt.co.uk/article/x-ray-sterilisation.
U.S. Appl. No. 14/776,088, filed Sep. 14, 2015, Collinson et al.
Kendall ULTEC Hydrocolloid Dressing (4"×4"), product ordering page, web page downloaded Jul. 13, 2014.
Protz, Kerstin: "Modern Wundauflagen unterstutzen Heilungsprozess", Wundversorgung: Indikation and Anwendung, Geriatrie Journal 4/05, pp. 3333-3339, with translation.

(56) References Cited

OTHER PUBLICATIONS

U.S. Appl. No. 61/828,604, filed May 29, 2013, Collinson et al.
U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
Product Data Sheet, WACKER SilGel 612 A/B. Jun. 2014.
Wacker SILPURAN 2445 data sheet, dated Oct. 11, 2014.
International Preliminary Report on Patentability, re PCT Application No. PCT/GB2011/001649, dated Jun. 6, 2013.
International Preliminary Report on Patentability, re PCT Application No. PCT/GB2011/001652, dated Mar. 18, 2013.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

\* cited by examiner

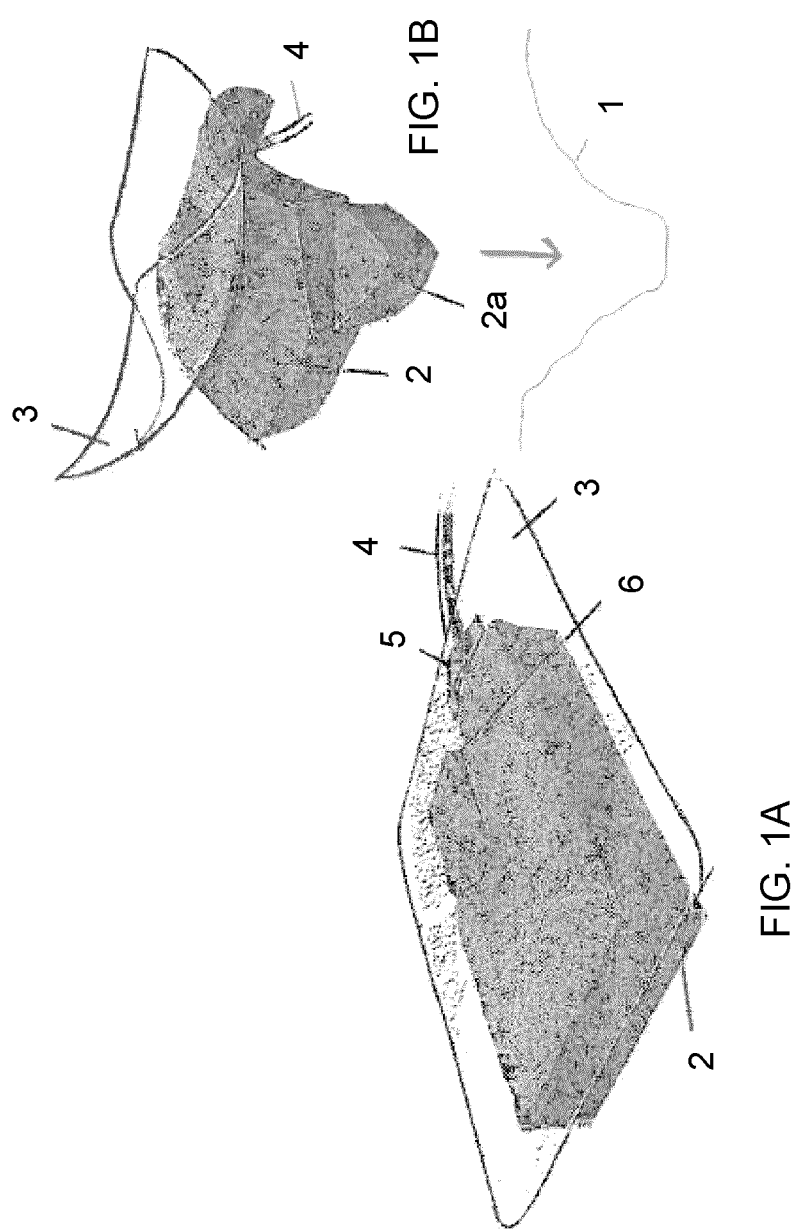

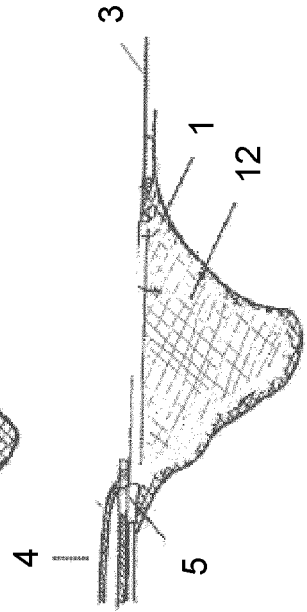
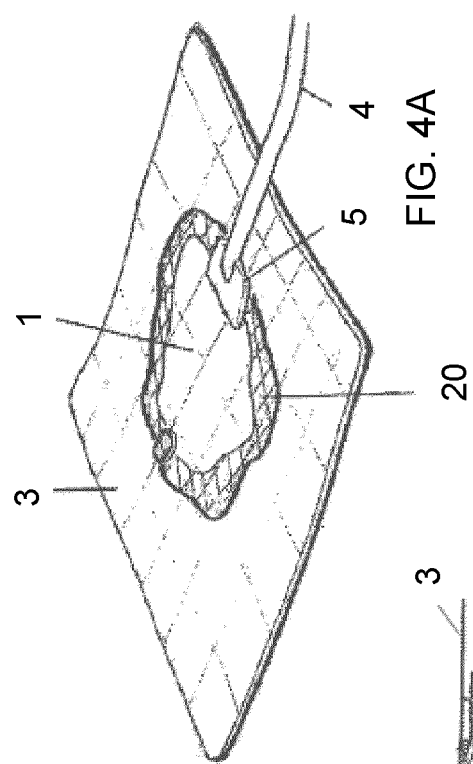
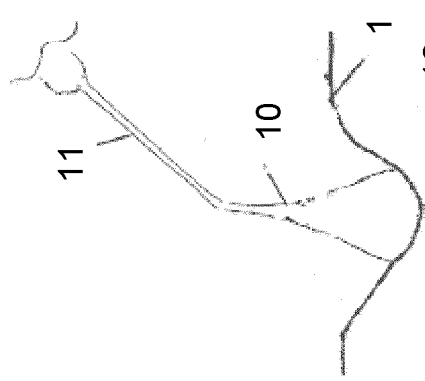
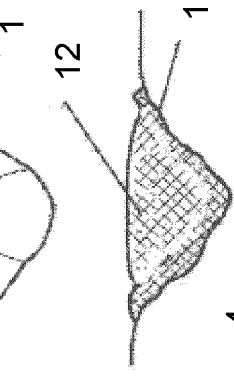
FIG. 3A
FIG. 3B
FIG. 3C
FIG. 4A

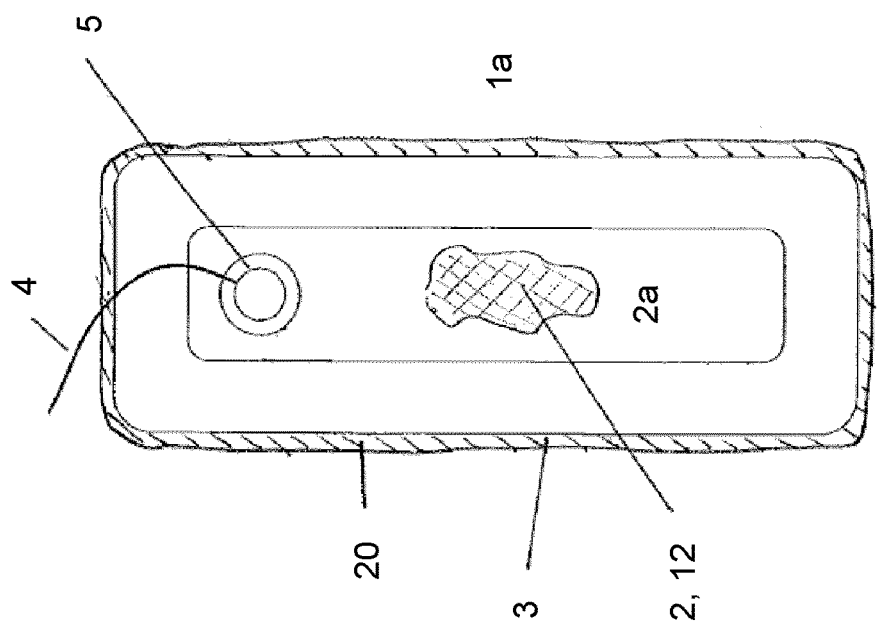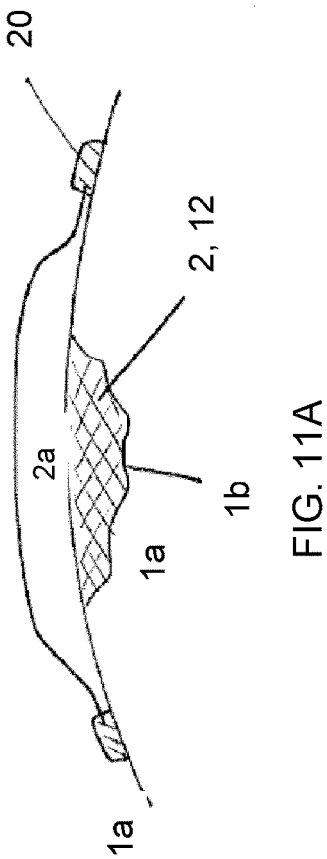
FIG. 11B
FIG. 11A

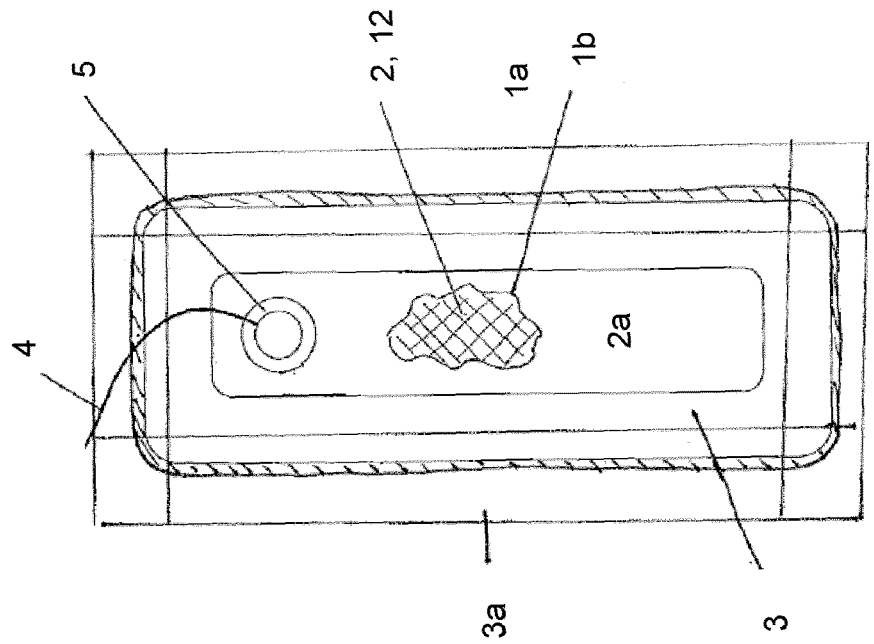
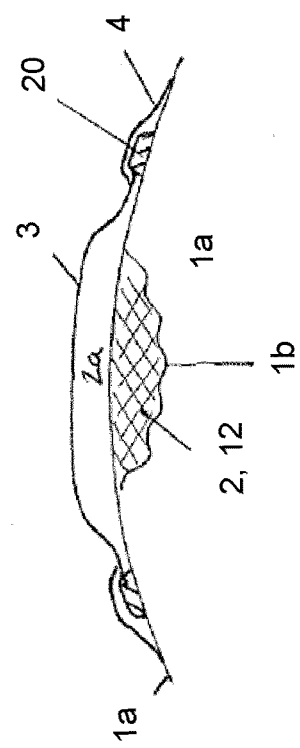
FIG. 12B
FIG. 12A

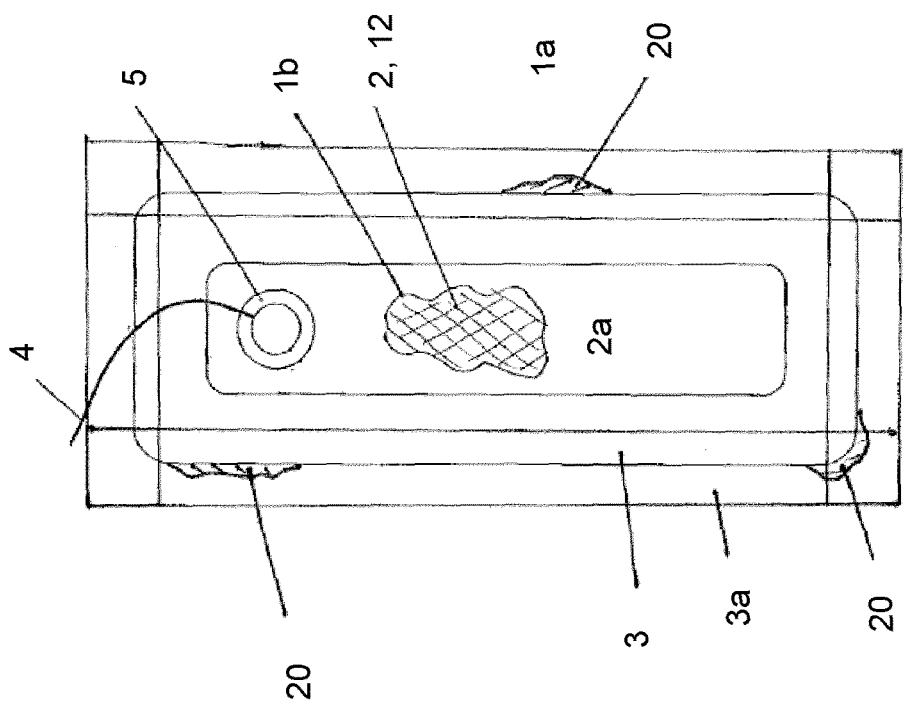
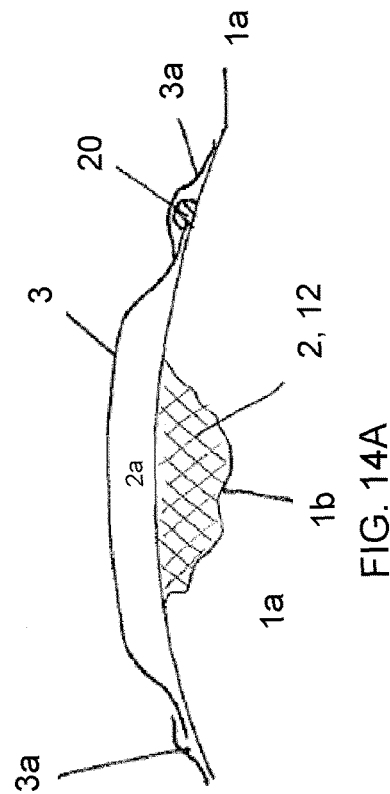
FIG. 14B
FIG. 14A

COMPOSITION I-II AND PRODUCTS AND USES THEREOF

CROSS-REFERENCE TO RELATED APPLICATIONS

This application is the U.S. National Phase application under 35 U.S.C. § 371 of International Application PCT/GB2011/001652, filed Nov. 25, 2011, which claims priority to Great Britain Patent Application No. 1019997.4, filed Nov. 25, 2010, and Great Britain Patent Application No. 1104512.7, filed Mar. 17, 2011.

BACKGROUND OF THE DISCLOSURE

Field of the Disclosure

Embodiments of the present invention relate to a two part, curable composition, methods for preparing the composition, manufacture thereof and methods for sterilisation thereof, medical and non-medical use thereof, methods for use or therapy therewith, a device incorporating the composition, and a precursor therefor including its sterilisable precursor composition. In particular certain embodiments relate to a sterilisable or sterile composition for medical use, particularly in wound therapy, more particularly as a wound packing material or filler which can be shaped and configured to the shape of a wound, or an adhesive or sealant for a wound dressing, most particularly for application in negative pressure wound therapy (NPWT).

Background

NPWT is a relatively new treatment for open wounds. Briefly, negative pressure therapy can assist in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilise the tissue in the apposed position of closure. A further beneficial use of TNP therapy can be found in grafts and flaps where removal of excess fluid is important and close proximity of the graft to tissue is required in order to ensure tissue viability. Typically in NPWT the wound cavity or surface is filled or covered with a material that allows the transmission of a partial vacuum (i.e. does not completely collapse) to the wound bed when a negative pressure is applied to the wound area, and also allows fluids to pass from the wound bed towards the source of negative pressure. There are two primary approaches to NPWT, i.e. gauze or foam types. The gauze type involves the use of a drain wrapped in gauze topped by a sealed dressing. The foam type involves the use of foam placed over or in the wound, also topped by a sealed dressing. One embodiment is directed primarily towards the foam type of NPWT. Further embodiments are directed towards either the foam or gauze type of NPWT, or to a further type of NPWT which uses a sealed dressing as a combination or preformed with additional absorption or distribution layers or the like.

A good material the foam based NPWT which offers good resistance to compression under loading, is hydrophobic, reticulated polyurethane foam of high free internal volume.

However articles of high free internal volume tend to be poorly drapeable due to the requirement for their structure to mechanically support their high free internal volume, and this is the case in foams applied in NPWT.

Therefore packing material for use in NPWT must be shaped to fit the wound to be packed. This is typically achieved by the medical practitioner (physician or nurse) cutting a preformed block of foam to approximately fit the wound using a scalpel, knife or scissors. This operation can be complex and has the potential to introduce contamination, moreover is time consuming and messy for the medical practitioner, and indeed can be dangerous with the possibility of particulate foam contaminating the wound site or of an accident during the cutting process. Accordingly the process of shaping the wound dressing is currently an unaddressed problem in the field of NPWT.

Castable compositions are known for use in wound care. WO2009/156709 discloses a topical negative pressure, or vacuum, wound therapy wound covering element or drape constructed of silicone or polyurethane based materials, which provides a substantially air-tight seal over a wound, having a vacuum connection tube or line for connection to a negative pressure source moulded or glued in place to reduce the likelihood of negative pressure leakage. The drape may be manufactured by casting a two-part heat curable silicone elastomer over the vacuum line, located in a mould. The resulting drape may be sterilised by irradiation and packaged in sterile form until required for use by placing over a foam or gauze wound filler.

An RTV-2 (addition cure two-part room temperature vulcanizing) silicone foam wound dressing, Cavi-Care, is sold non-sterile. U.S. Pat. No. 5,153,231 discloses the composition which is capable of providing a low density foamed medical dressing by releasing two components into a mixing vessel by rupture of their individual packaging, mixing and dispensing or casting onto a surface such as an open wound and allowing the mixture to cure at room temperature.

It would be useful to provide a castable in-situ wound filler in the form of an RTV-2 silicone foam. It would also be useful to provide a castable in-situ adhesive or sealant for a NPWT drape or dressing. The problem is that for an RTV-2 wound filler, adhesive, sealant or the like to be viable the two part system must be available sterile.

Where a product for medical use is required to be sterile at point of use, it is a well accepted principle that it should be manufactured using aseptic processing only when terminal sterilisation is not feasible. To ensure the highest levels of sterility assurance for a medical product, it should therefore be terminally sterilised in its final packaging.

Although sterile foamed wound dressing materials are available such as Allevyn™, a polyurethane foam wound covering element, and black foam ("Granufoam"), a polyurethane wound filler, supplied packaged in a peel pouch, no two-part RTV-2 silicone composition or indeed any RTV-2 composition, foamable or otherwise, appears to be available sterile, as the two part system prior to curing, either terminally sterilised in primary packaging or sterilised and then aseptically packaged. Furthermore a process for sterilising these systems does not appear to be available.

One object of the invention is to provide an improved terminally sterile RTV-2 foamable silicone composition. It is a further object to provide an improved, terminally sterile, wound filler which can be conformed to the shape of a wound cavity. It is a further object to provide a terminally sterile RTV-2 non-foamable or partially foamable silicone composition. It is a further object to provide a terminally sterile adhesive or sealant which can be conformed about a wound cavity.

In attempting to find a route to sterilise a two part foamable curable silicone composition which could be cast into a desired shape and cured in situ to form a shaped three dimensional body, we found that most of the sterilisation techniques that would be typically employed to sterilise a material are unsuitable or are incapable of sterilising the composition without degradation. The same was true in attempting to find a route to sterilise a two part adhesive or sealant.

Established terminal sterilisation procedures give a $10^6$ confidence in sterility. An attractive route for sterilisation appeared to be irradiation. This presents a cost-effective route for which requisite packaging is readily available.

25 kGy is a typical dose for achieving the required level of microbial kill for terminal sterility. However on gamma irradiating at 25 kGy, Rhodorsil RTFoam 3240, a RTV-2 polydiorganosiloxane composition having liquid prepolymer mixture Part A and Part B, suffered a noticeable increase in viscosity in Part A whilst Part B formed a solid elastomer. The resulting sterile composition was clearly incapable of mixing and casting.

This viscosity increase can be influenced by reducing the gamma irradiation dose levels to 15 kGy and even 10 kGy, however across a wide range of gamma doses the irradiation alters the physical properties of the composition Part, with an increase in viscosity being observed at all dose levels.

SUMMARY OF SOME EXEMPLIFYING EMBODIMENTS

We have now suprisingly found a route for sterilisation of packaged RTV-2 compositions, for which the composition is capable of withstanding irradiation doses sufficient for sterilisation, without degradation thereof.

Accordingly, there is provided according to a first embodiment of the present invention a curable composition comprising or apportioned between at least one Part A and at least one Part B, the at least one Part A comprising:
(i) one or more alkenyl-containing prepolymers having at least one alkenyl group or moiety per molecule,
and the at least one Part B comprising:
(ii) one or more SiH-containing prepolymers having at least one Si—H unit or moiety per molecule;
the composition additionally comprising:
(iii) a catalyst for curing by addition of alkenyl-containing prepolymer (i) to SiH-containing prepolymer (ii),
wherein prepolymer (ii) is substantially absent from Part A and prepolymer (i) is substantially absent from Part B. Preferably the Parts are sealed within barrier means in manner to prevent contamination thereof, In a further preferred embodiment of the invention there is provided a curable composition for use as a negative pressure wound therapy wound filling material, the composition comprising or apportioned between at least one Part A and at least one Part B, the at least one Part A comprising:
(i) one or more alkenyl-containing prepolymers having at least one alkenyl group or moiety per molecule,
and the at least one Part B comprising:
(ii) one or more SiH-containing prepolymers having at least one Si—H unit or moiety per molecule;
the composition additionally comprising:
(iii) a catalyst for curing by addition of alkenyl-containing prepolymer (i) to SiH-containing prepolymer (ii),
wherein prepolymer (ii) is substantially absent from Part A and prepolymer (i) is substantially absent from Part B
wherein the at least one Part A and at least one Part B are adapted to be dispensed in cooperative manner facilitating intimate contact and curing thereof and formation of a porous foam which is capable of transmitting negative pressure. Alternatively the composition may be useful as a negative pressure wound therapy adhesive or sealant, which is capable of adhering a negative pressure wound therapy drape or which is air-tight. Preferably the Parts sealed within barrier means in manner to prevent contamination thereof, In the above embodiments, catalyst may be present in an inert Part, or preferably in the at least one Part A. Suitably the at least one Part A and/or the at least one Part B is sterilisable by irradiation or sterilised by irradiation, or one thereof is sterilisable by irradiation or sterilised by irradiation and the other thereof is sterilisable or sterilised by other means.

In the above embodiments, the phrase "prepolymer . . . is substantially absent from" denotes that no detectable amount of the defined prepolymer is present in the defined Part, or if present, the amount thereof is insufficient to cause an increase in viscosity of the Part which would cause the respective Parts to be incapable of intimate contact, for example of flow for the purpose of dispensing and mixing, in manner to form a cured product. Preferably prepolymer (i) makes up substantially the entirety of reactive prepolymer present in Part A which is capable of undergoing a hydrosilylation reaction and prepolymer (ii) makes up substantially the entirety of reactive prepolymer present in Part B which is capable of undergoing hydrosilylation reaction. More preferably prepolymer (i) and/or (ii) makes up substantially the entirety of reactive prepolymer present in Part A and/or Part B respectively.

Whilst it is clear that prepolymers incorporate a number of different molecules differing in chain length and unit composition, and that a reactive prepolymer other than (i) or (ii) may be present in trace amount, certain embodiments encompass compositions for which such trace amount is insufficient to react with prepolymer (i) or (ii) comprised in the same Part, in the course of irradiation sterilisation, for example to an extent that the viscosity of the Part is increased by a value of greater than 0% up to 5% by weight and/or the foam properties are affected by a volume reduction greater than 0% up to 5%. For example therefore the Part not incorporating catalyst, such as Part B, may incorporate a trace amount of prepolymer (i) greater than 0% up to 5% by weight. Part A, if not incorporating catalyst, may incorporate a trace amount of prepolymer (ii) greater than 0% up to 5% by weight, however this is not preferred. Preferably prepolymer (ii) is totally absent from Part A.

Prepolymers include a distribution of discrete polymer chains with differing numbers of reactive groups. Accordingly a more accurate measure of trace amount of one Part in another is given by ratio of reactive groups. Accordingly we have found that Part B may incorporate a trace amount of prepolymer (i) represented as molar ratio (Si—H unit or moiety)/(alkenyl unit or moiety) of greater than or equal to 2000, preferably greater than or equal to 5,000 more preferably greater than or equal to 10,000.

We have surprisingly found that the at least one Part A, and preferably both of the at least one Part A and at least one Part B are suitable for being subjected to an irradiation dose sufficient for terminal sterilisation thereof.

Reference herein to barrier means for the prevention of contamination of respective Parts A and B is to any chemical or mechanical barrier which prevents contamination by infectious agents which are capable of proliferation, or by contaminants which are capable of reaction with the prepolymers (i) and/or (ii), or otherwise prevents passage of substances which deleteriously affect the reaction of Parts A and B, for example loss of composition components by leakage. Preferably the barrier means is capable of preventing contamination by microorganisms or viruses, more preferably by pathogenic microbes or viruses, and escape of composition components.

We have surprisingly found that while a standard irradiation cycle will not sterilise commercially available compositions without degrading their ability to form a cured polymer having desired properties, modified compositions will withstand such a cycle and are emminently suited for providing a terminally sterile RTV-2 composition, hitherto unknown and unavailable.

Embodiments of the invention may have application to any RTV, LTV or HTV compositions, which may comprise 2 or more components or Parts. Preferably the composition of the invention is an RTV-2, LTV-2 or HTV-2 composition, foamable or otherwise, for any envisaged use requiring sterility. The addition cure chemistry of 2-part RTV, LTV and HTV compositions is based on the hydrosilylation of vinyl functional prepolymers by Si-hydride functional prepolymers. Room temperature vulcanising is typically taken to mean the system cures below 50° C. Low temperature vulcanising is taken to mean the system cures in the range from 50° C. to 130° C. High temperature vulcanising is taken to mean the system cures at a temperature in excess of 130° C. More preferably the composition is an RTV-2 composition.

Embodiments of the invention may also have application to any two or more Part curable composition for which the Parts are adapted to be dispensed or released in cooperative manner facilitating intimate contact and curing thereof. Such Parts are therefore suitably fluid phase or capable of fluid behaviour under acceptable dispensing or release conditions or capable of wetting out a surface or material to which they are dispensed or released, for example Part A and Part B are capable of mutual wetting out when cooperatively dispensed or cooperatively released.

Suitably the at least one Part A and at least one Part B are sealed within or upon at least two respective receptacles or supports and are adapted to be dispensed or released therefrom in cooperative manner facilitating intimate contact and curing thereof. Suitably the receptacles or supports are antimicrobially sealed.

The Part A and Part B may be provided sealed within receptacles or on supports in substantial absence of air within the receptacles or on the supports.

Reference herein to Parts A and B being present in receptacles in substantial absence of air or moisture, is suitably to air or moisture presenting less than 10% of the receptacle volume, preferably less than 5% of the receptacle volume. Air or moisture is suitably absent from any space above or about the composition, i.e headspace or the like, or such space is substantially absent. Air or moisture may additionally be absent from the composition itself, i.e the composition may be degassed or sparged or the like to remove air. It will be appreciated that the objective of providing an absence of air is to provide an absence of oxygen and moisture vapour.

Accordingly a substantial absence of air may be provided in known manner by displacement and/or removal or air. Displacement of air is suitably by means of purging the space about the composition, such as the headspace present above the composition within the barrier means, with a suitable inert gas; and/or sparging the composition with a suitable inert gas. Removal of air is suitably by means of providing the Part in a receptacle of substantially equal volume to the Part volume in manner to substantially eliminate any headspace. A suitable inert gas is argon or nitrogen or the like. Purging displaces air above the Part with inert gas. Sparging displaces air within the Part with inert gas. Matching volumes removes air above the Part.

Receptacles or supports preferably comprise any suitable material which provides a barrier means as hereinbefore defined, preferably to microbial or viral infection and to ingress or egress of chemically reactive or contaminating material. Suitably receptacle or support materials are selected from any irradiation tolerant material, preferably any gamma, x-ray or e-beam irradiation tolerant material, which is sufficiently dense to be impermeable to contaminants, suitably being non-porous to such contaminants. Receptacle or support material may comprise any commonly available packaging materials and is preferably selected from polymeric materials such as polyolefins for example polyethylene (PE), polyethylene terephthalate (PET) and polypropylene (PP), polystyrene (PS), polyamides, and the like, metals such as metal foils, glass, silicone materials and from composites, laminates and combinations thereof; more preferably is selected from PE, PET and PP.

Suitably the composition including receptacles or supports and any integral cooperating means is packaged in a further outer (secondary) packaging which is resistant to EO or is steam permeable, which is suitable for sterilisation in usual manner. Thereby both the interior and exterior of the composition are maintained sterile, and can be carried into a sterile field and opened.

A receptacle or support may be flexible or rigid. A rigid receptacle or support is suitably any vial or cartridge as known in the art. A flexible receptacle or support for example may be formed from a laminate of metal foil having on each face thereof a film of polymer as hereinbefore defined which can be heat-sealed or laminated.

A receptacle may comprise a portion which is intended for mechanical opening, rupture or penetration in manner to release the composition Part sealed therein. A receptacle may therefore comprise a combination of different materials or a combination of different, rupturable or penetratable and non-rupturable or non-penetratable, thicknesses of a material.

Receptacles may be manually ruptured at weakened portions thereof, or mechanically ruptured or penetrated by physical means for example provided in a device for penetration and cooperative dispensing of composition parts. Suitable physical means include needles, spikes, punches such as bayonet caps, push-fit opening means and the like.

Reference to cooperative dispensing as hereinbefore defined is to any method by which one or more Parts is dispensed simultaneously with and into direct contact with the other one or more Parts, preferably with simultaneous mixing. Preferably receptacles are adapted to be received within a device providing means to cooperatively release the respective Parts into an of enhancing accuracy of administering composition.

Preferably the composition is suitable for dispensing into or about a wound. Preferably the composition is suitable for dispensing or releasing in a sterile field or environment. This is particularly advantageous in the case of medical applications for example within the sterile field of an operating theatre allowing the possibility to dispense directly or indirectly, for example via a mould, into a wound in a sterile field or environment. This avoids the need to contact the composition once dispensed, for example for positioning or shaping, and minimises the risk of introducing infection.

An embodiment of the RTV-2 composition of the invention may comprise any prepolymers that follow a hydrosilylation reaction. One prepolymer contains alkenyl groups, the other contains Si—H moieties. The group of siloxane polymers is based on a structure comprising alternate silicon and oxygen atoms with various organic moieties attached to the silicon. Curing can be defined as a treatment that decreases the flow of an elastomer. This change is generally brought about by linking reactions between polymer molecules. Where the silicon hydride (Si—H) moiety is part of a polysiloxane, it is possible for the alkenyl group to either be part of a siloxane prepolymer or otherwise part of a non-siloxane prepolymer. The position of the alkenyl functional group is not critical and it may be either at the molecular chain terminals or in non-terminal positions along the molecular chain.

Prepolymers (i) and (ii) are commercially available or may be obtained by known techniques. Suitably prepolymers (i) and/or (ii) are independently selected from known and novel fluid phase and soluble homopolymeric, and copolymeric prepolymers, and their entangled systems and mixtures thereof. The compositions, in turn, cure to form copolymers, and may also include their entangled systems and mixtures with other non-reactive prepolymers if present in the composition. By fluid phase is meant that the prepolymers are capable of admixture to form the respective Part. Preferably the respective Parts are of a viscosity suitable for mixing by hand within a period of up to 1 minute.

The term fluid phase is intended to include prepolymers which can exist in fluid phase or behave as fluids, i.e the sterilised prepolymers are capable of admixture to form the respective Part.

Copolymeric prepolymers include all hybrids derived from two or more monomeric species, including alternating, periodic, statistical, random, block, linear, branched, star, graft and pendant copolymers. Entangled systems include interpenetrating networks (IPNs) and semi-interpenetrating networks (SIPNs). It is also the case that these prepolymers can incorporate both organic and inorganic moieties.

Preferably prepolymers (i) and (ii) are selected from silicones, including siloxanes and modified siloxanes, polyurethanes (PU) including polyester and polyether urethanes, elastomeric polyether polyesters, polyglycolic acid, polyacetates such as ethyl vinyl acetate, polyacrylate, polyacid derivatives of polysaccharides, such as carboxyalkylcellulose, carboxyalkylchitosan and copolymers thereof, and their hybrids including copolymers, entangled systems and mixtures thereof.

More preferably the curable composition makes use of an addition cure reaction between organohydrogensiloxane units and organoalkenylsiloxane units. These units may be incorporated into a wide range of polymeric, copolymeric, entangled and mixed prepolymers as hereinbefore defined. Preferred siloxane prepolymers (i) and (ii) therefore include these respective units and are more preferably polyorganosiloxanes.

Examples of hybrid organic-inorganic polymeric systems that have used both siloxane and organic units include: acrylate functionalized siloxane copolymers, which have found use in contact lenses (U.S. Pat. No. 3,808,178); hybrid grafts where organic polymers are grafted onto a polysiloxane chain or where siloxanes are grafted onto organic polymers, for example in silane graft technology for cross linkable HDPE (U.S. Pat. No. 3,646,155) where hybrid grafts have been used to allow the cross linking of organic polymers through siloxane bond formation; hybrid block copolymers for example silicone-polycarbonate block copolymers (U.S. Pat. No. 3,274,155); and copolymers of hybrids of silicone and ethylene copolymers, cross-linked with vinyl-containing silicone copolymers which have found use in coating textiles (US 2005/0100692);

IPNs represent a special class of hybrid polymeric systems, these systems use a combination of mechanical entanglement and crosslinking in which one polymer is cured about another; these include thermoplastics entangled with platinum catalyzed addition cure silicones such as silicone-urethane IPNs and semi-IPNs including silicone-urethane and silicone-polyamide systems which are of general application or have found specific use in coating textiles (U.S. Pat. Nos. 4,714,739, 7,543,843); hydrophilic components immobilised in a silicone polymer (U.S. Pat. No. 5,397,848) which have found use as contact lens material; and silicone polymer cured about a non-reactive polymer of comparable adhesion, which have found use in coating textiles (U.S. Pat. No. 7,132,170).

Prepolymers may also be selected from modified silicones (MS) which find use as adhesives in catheter tubing and the like.

Preferred compositions comprise a polydiorganosiloxane prepolymer (i) and/or (ii) and/or their respective combinations with the aforementioned prepolymers. A composition in which prepolymers comprise or consist essentially of polydiorganosiloxane prepolymers (i) and (ii) has particular advantages, for example in applications where low toxicity is an advantage, preferably in medical or dental applications or in non-medical or non-dental applications requiring low toxicity or favorable biocompatibility.

Prepolymer (i) and (ii) may comprise respective alkenyl-containing units and organohydrogensiloxane units situated along the length of prepolymer chains, and/or as prepolymer chain end-capping units or a combination thereof. Prepolymer (i) in-chain and end-capping alkenyl units preferably comprise alkenyl group or moiety $R^{Alk}$ selected from $C_{2-20}$ alkenyl optionally substituted or including one or more aryl groups or moieties. $R^{Alk}$ may comprise terminal or non terminal unsaturation, and may be of the formula i-I:

$$-R^{Alk1}-CR^{Alk1}=CR_2^{Alk2} \qquad \text{(i-I)}$$

in which the groups $R^{Alk1}$ and $R^{Alk2}$ are independently selected from H, $C_{1-20}$ alkyl and $C_{5-20}$ aryl groups and combinations thereof and a moiety $R^{Alk1}$ is selected from a single bond, $C_{1-20}$ alkyl and $C_{5-20}$ aryl groups and combinations thereof. One of $R^{Alk2}$ may be a moiety linking to polymer chain. More preferably each $R^{Alk}$ is independently selected from vinyl, allyl, propenyl, and from terminally and non-terminally unsaturated butenyl, pentenyl, hexenyl, heptenyl, octenyl, nonenyl and decenyl groups, most preferably selected from vinyl and hexenyl groups.

Preferably prepolymer (i) comprises a polydiorganosiloxane polymer or copolymer comprising alkenyl-containing units of the formula (i-II):

$$\equiv Si-R^{Alk}, \qquad \text{(i-II)}$$

more particularly of the formula (i-III) and/or (i-IV):

$$-O-SiR^1R^{Alk}-O- \qquad \text{(i-III)}$$

$$-O-SiR^1_2R^{Alk} \qquad \text{(i-IV)}$$

wherein $R^{Alk}$ is as hereinbefore defined and one or more groups $R^1$ are organo groups suitably independently selected from alkyl and aryl groups, more preferably $C_{1-20}$ alkyl and $C_{5-20}$ aryl groups and combinations thereof, for example from methyl, ethyl, propyl, butyl, pentyl, hexyl, heptyl, octyl, nonyl and/or decyl groups and moieties.

More particularly prepolymer (i) is selected from the formula i-V and i-VI:

  i-V

  i-VI wherein $P^i$ denotes the remainder of the polymer chain which may incorporate same or different units, and $R^1$ is as hereinbefore defined.

Prepolymer (i) may also comprise a polyorganosiloxane exhibiting, per molecule, at least two $C_2$-$C_6$ alkenyl groups bonded to the silicon and having, for example, a viscosity of between 10 and 300 000 mPa·s, which can in particular be formed of at least two siloxyl units of formula:

  (III)

in which:
- Y is a $C_2$-$C_6$ alkenyl such as vinyl, allyl or hexenyl groups, preferably vinyl,
- R is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
- d is 1 or 2, e is 0, 1 or 2 and d+e=1, 2 or 3,
- optionally all the other units being units of average formula:

  (IV)

in which R has the same meaning as above and f=0, 1, 2 or 3.

Examples of prepolymer (i) are, for example, dimethylpolysiloxanes comprising dimethylvinylsilyl ends, (methylvinyl)(dimethyl)polysiloxane copolymers comprising trimethylsilyl ends or (methylvinyl)(dimethyl)polysiloxane copolymers comprising dimethylvinylsilyl ends.

A convention accepted in the art for denoting the units of silicones according to the number of oxygen atoms bonded to the silicon is used here. This convention uses the letters M, D, T and Q (abbreviations for "mono", "di", "tri" and "quatro") to denote this number of oxygen atoms. This nomenclature of silicones is described, for example, in the work by Walter Noll, "Chemistry and Technology of Silicones", Academic Press, 1968, 2nd edition, on pages 1 to 9.

Prepolymer (i) may also be a silicone resin bearing at least two alkenyl, preferably vinyl groups. Such silicone resin comprising at least two different siloxane units chosen from those of M siloxane unit of formula $R_3SiO_{1/2}$, D siloxane unit of formula $R_2SiO_{2/2}$, T siloxane unit of formula $RSiO_{3/2}$ and Q siloxane unit of formula $SiO_{4/2}$, wherein R denotes a monovalent hydrocarbon group, with the conditions that at least one of these siloxane units being a T or Q siloxane unit and that at least two of the M, D and T siloxane units comprises an alkenyl group.

The silicone resin could be selected from the group consisting of:
an organopolysiloxane resin of formula $MT^{Vi}Q$ consisting essentially of:
  (a) trivalent siloxane units $T^{Vi}$ of the formula $R'SiO_{3/2}$;
  (b) monovalent siloxane units M of the formula $R_3SiO_{1/2}$, and
  (c) tetravalent siloxane units Q of the formula $SiO_{4/2}$
an organopolysiloxane resin of formula $MD^{Vi}Q$ consisting essentially of:
  (a) divalent siloxane units $D^{Vi}$ of the formula $RR'SiO_{2/2}$;
  (b) monovalent siloxane units M of the formula $R_3SiO_{1/2}$, and
  (c) tetravalent siloxane units Q of the formula $SiO_{4/2}$
an organopolysiloxane resin of formula $MDD^{Vi}Q$ consisting essentially of:
  (a) divalent siloxane units $D^{Vi}$ of the formula $RR'SiO_{2/2}$;
  (b) divalent siloxane units D of the formula $R_2SiO_{2/2}$
  (b) monovalent siloxane units M of the formula $R_3SiO_{1/2}$, and
  (c) tetravalent siloxane units Q of the formula $SiO_{4/2}$
an organopolysiloxane resin of formula $M^{Vi}Q$ consisting essentially of:
  (a) monovalent siloxane units $M^{Vi}$ of the formula $R'R_2SiO_{1/2}$; and
  (b) tetravalent siloxane units Q of the formula $SiO_{4/2}$, and
an organopolysiloxane resin of formula $M^{Vi}T^{Vi}Q$ consisting essentially of:
  (a) monovalent siloxane units $M^{Vi}$ of the formula $R'R_2SiO_{1/2}$;
  (b) trivalent siloxane units $T^{Vi}$ of the formula $R'SiO_{3/2}$, and
  (c) tetravalent siloxane units Q of the formula $SiO_{4/2}$
wherein R denotes a monovalent hydrocarbon group such as methyl and R' denotes a vinyl group:

Such resins are well-known branched organopolysiloxane oligomers or polymers which are commercially available. They are provided in the form of solutions, preferably siloxane solutions.

Prepolymer (ii) in-chain and end-capping polyorganohydrogensiloxane units are preferably selected from the formula ii-I and ii-II:

  ii-I

  ii-II more preferably prepolymer (ii) is selected from formula ii-III and ii-IV:

  ii-III

  ii-IV $P^{ii}$ denotes the remainder of the polymer chain which may incorporate same or different units and one or more groups $R^2$ are organo groups suitably independently selected from $C_{1-20}$ alkyl, $C_{5-20}$ aryl and combinations thereof, for example from methyl, ethyl, propyl, butyl, pentyl, hexyl, heptyl, octyl, nonyl and/or decyl groups.

Prepolymer (ii) preferably comprises a polyorganohydrogensiloxane-polydiorganosiloxane copolymer, incorporating one or more units ii-I and/or ii-II:

  ii-I

  ii-II and one or more units ii-V and/or ii-VI:

  ii-V

  ii-VI wherein $R^2$ is as hereinbefore defined, more preferably copolymer incorporating polyorganohydrogensiloxane endcapping units, i.e prepolymer chains terminate with the group or moiety ii-VII:

$$\equiv Si-H, \qquad \qquad \text{ii-VII}$$

more particularly with the unit of formula ii-II:

$$-O-SiR^2{}_2H \qquad \qquad \text{ii-II}$$

as hereinbefore defined. Most preferably prepolymer (ii) comprises methylhydrogensiloxane-dimethylsiloxane copolymers.

Prepolymer (ii) may also comprises a polyorganosiloxane, exhibiting, per molecule, at least two hydrogen atoms bonded to the silicon and preferably at least three $\equiv$SiH units and having, for example, a viscosity of between 1 and 5000 mPa·s, which can in particular be formed of siloxyl units of formula:

$$H_g X_i SiO_{\frac{4-g-i}{2}} \qquad (V)$$

in which:
X is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
g=1 or 2, preferably =1, i=0, 1 or 2 and g+i=1, 2 or 3, optionally all the other units being units of average formula:

$$X_j SiO_{\frac{4-j}{2}} \qquad (VI)$$

in which X has the same meaning as above and j=0, 1, 2 or 3.

Examples of prepolymer (ii) are polymethylhydrosiloxanes or methylhydrodimethylsiloxane copolymers.

Alternatively or additionally prepolymers (i) and (ii) are as defined in U.S. Pat. No. 5,153,231 for Cavi-Care RTV-2 type compositions, also as defined in US 2006/0217016, U.S. Pat. Nos. 3,928,629 and 4,529,553, 4,714,739 and US 2002/0010299 the contents of which are incorporated herein by reference, or as commercially available (Rhodorsil RTFoam 3240, Mepiseal, Silpuran 2111 A/B, Silpuran 2400/18 A/B, and the like.

In the case that prepolymers include other units additional to iIII, iIV, iiI and iiII for example, these are suitably not reactive with the respective prepolymer at ambient temperature or under sterilising conditions.

Suitably the ratio of silicon-bonded hydrogen atoms provided by (ii) to silicon-bonded alkenyl moieties provided by (i) is at least 0.5:1, preferably 1:1, Preferably embodiments of the curable composition follow the catalysed addition cure reaction according to the following scheme:

$$P^i-R^{Alk1}-CR^{Alk1}=CR^{Alk2}{}_2+P^{ii}-SiHR^2R^{2/P} \xrightarrow{[catalyst]}$$

$$P^i-R^{Alk1}-CHR^{Alk1}CR^{Alk2}{}_2-SiR^2R^{2/P}P^{ii}$$

more preferably:

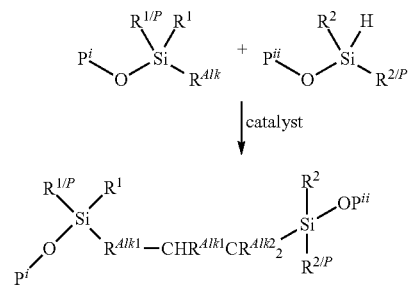

wherein integers are as hereinbefore defined and $R^{1/P}$ is selected from $P^i$ and $R^1$ as hereinbefore defined and $R^{2/P}$ is selected from $P^{ii}$ and $R^2$ as hereinbefore defined.

Suitably the prepolymers (i) and (ii) and catalyst (iii) are apportioned in at least one Part A and at least one Part B in manner to provide respective Parts A and B which in isolation are not reactive at ambient temperature, nor under sterilisation conditions. Apportioning may also be determined according to volume and viscosity. The at least one Part A and at least one Part B may be of substantially equal volume and viscosity or of different volume and/or viscosity. Part A or Part B may incorporate a suitable viscosity moderator or diluent, in amount to increase or reduce volume and/or viscosity. By this means Part A and Part B having different volume and viscosity may be volume and viscosity matched for improved ease and intimacy of mixing and dispensing. A suitable diluent is for example a silicone oil which is available in any desired viscosity for thickening or thinning effect. Advantageously we have found that Part A comprising a silicone oil is radiation sterilisable without deleterious effect on properties of the resultant cured composition.

In the case that Part A is of greater volume and higher viscosity than Part B, Part A may be apportioned between two or more Parts A1, A2 etc, of equal volume, providing 3 or more Parts A and B of approximately equal volume. Alternatively or additionally Part B may incorporate silicone oil as a substantially inert diluent and/or thickener.

A catalyst as hereinbefore defined may be any catalyst which is effective in catalysing the addition curing reaction as hereinbefore defined, more preferably as hereinabove illustrated. Suitable catalysts are selected from any known form of platinum, rhodium, palladium, nickel and like addition curing hydrosilylation catalysts, for example as disclosed in U.S. Pat. No. 5,153,231, US 2006/0217016, U.S. Pat. Nos. 3,928,629 and 4,529,553 the contents of which are incorporated herein by reference.

A platinum catalyst may be selected from platinum black, platinum as deposited on carriers including silica such as silica gel or carbon such as powdered charcoal, platinic chloride or chloroplatinic acid and alcohol solutions thereof, salts of platinic and chloroplatinic acids and platinum complexes such as platinum/olefin, platinum/alkenylsiloxane, platinum/beta-diketone, platinum/phosphine and the like. Chloroplatinic acid may be the hexahydrate or anhydrous form. A platinum complex may be prepared from chloroplatinic acid and its hexahydrate, or from platinous chloride, platinum dichloride, platinum tetrachloride and their neutralised complexes with divinyltetramethyldisiloxane, optionally diluted with dimethylvinylsiloxy endcapped polydimethylsiloxane.

A palladium catalyst may be selected from palladium on carbon, palladium chloride and the like.

A rhodium catalyst may be selected from rhodium chloride and one or more complexes of rhodium having the general formula iii-I or iii-II:

 (iii-I)

 (iii-II)

wherein each X represents a halogen atom and each R represents an alkyl or aryl radical or combination thereof having from 1 to 8 inclusive carbon atoms or the $R'_3SiQ$ group in which Q represents a divalent aliphatic hydrocarbon radical having from 1 to 6 inclusive carbon atoms and R' represents an alkyl or aryl radical or combination thereof having from 1 to 8 inclusive carbon atoms or a $(CH_3)_3Si$— group, not more than one R' per molecule being $(CH_3)_3Si$—. For example rhodium chloride/di(n-butyl)sulfide complex and the like.

A nickel catalyst is preferably a zero valent nickel selected from $M_2Ni^{(0)}$ such as bis(1,5-cyclo-octadienyl) nickel ($Ni(COD)_2$) and from $MNi^{(0)}G$ wherein M is a bidentate alkene cyclic hydrocarbon ring of $C_{8-12}$ and G is selected from monodentate and bidentate phosphorous groups having hydrogen atoms, substituted or unsubstituted hydrocarbon radicals or mixtures thereof bonded to the phosphorous atoms of the phosphorous groups.

The composition may include a catalyst inhibitor. Suitable inhibitors are known in the art. For example a catalyst inhibitor may be selected from a polymethylvinylsiloxane cyclic compound and an acetylenic alcohol, such as methyl butynol for example as in Cavi-Care Preferably the composition comprises an addition-reaction retardant or a crosslinking inhibitor chosen, for example, from the following compounds:
  polyorganosiloxanes substituted with at least one alkenyl that may optionally be in cyclic form, tetramethylvinyltetrasiloxane being particularly preferred,
  organic phosphines and phosphites,
  unsaturated amides,
  alkyl maleates, and
  acetylenic alcohols.

These acetylenic alcohols (see FR-A-1 528 464 and FR-A-2 372 874), which are among the preferred thermal blockers of the hydrosilylation reaction, have the formula:

in which formula
  R' is a linear or branched alkyl radical, or a phenyl radical;
  R" is H or a linear or branched alkyl radical, or a phenyl radical; the radicals R', R" and the carbon atom alpha to the triple bond possibly forming a ring; and
  the total number of carbon atoms contained in R' and R" being at least 5 and preferably from 9 to 20.
  Examples that may be mentioned include:
  1-ethynyl-1-cyclohexanol;
  3-methyl-1-dodecyn-3-ol;
  3,7,11-trimethyl-1-dodecyn-3-ol;
  1,1-diphenyl-2-propyn-1-ol;
  3-ethyl-6-ethyl-1-nonyn-3-ol;
  2-methyl-3-butyn-2-ol;
  3-methyl-1-pentadecyn-3-ol.

These α-acetylenic alcohols are commercial products. Such a retardant is present in a maximum proportion of 3000 ppm relative to the total weight of the polyorganosiloxanes in the silicone composition. Methyl butynol could be chosen as in Cavi-Care.

The composition may be non-foamable or may be foamable, comprising (iv) a blowing agent, selected from any agent which evolves gas or vapour as part of or during the curing reaction, for example selected from H-donors, OH-containing agents, H-bonding agents such as:
  alcohols including methanol, ethanol, n-propanol, isopropanol, n-butanol, 2-butanol, tert-butanol, n-hexanol, n-octanol and benzyl alcohol. n-Propanol, n-butanol, n-hexanol and n-octanol are particularly preferred,
  polyols such as diols including, 4-butanediol, 1,5-pentanediol and 1,7 heptanediol,
  silane or polysilane having at least one silanol group, or water.

A foamable composition may produce a foam having any desired porosity or pore architecture. In a particular advantage a foamable composition provides an open-pore foam. A preferred foamable composition is adapted to deliver a foam of very high free internal volume, e.g. of the order of 70% to 90%. Preferred porous foams are of mechanical strength to prevent the foam structure collapsing in use, more preferably are adapted to form a cured three dimensional body which is resiliently deformable.

Preferably a foamable composition is adapted to deliver a foam which cures to form open interfaces with moist or wet surfaces. Such open-interface foams are suitable for communicating with wound surfaces via the foam body, for example. In a particular advantage we have found that such open-interface foams are provided by silicone compositions. In a further advantage the composition is suitable for providing a cured porous three dimensional body of desired shape.

When the composition is non foamable it could lead after hydrosilylation to a silicone elastomer or to a silicone gel. Within the meaning of the present invention, the term "silicone gel" denotes a crosslinked silicone product characterized by a degree of penetration of, for example, between 20 and 500 tenths of a mm (measured by ASTM D 2137 penetrometry, weight of the rod and of the cone: 62.5 g).

When the composition is prepared for a silicone gel it may have at least one nonfunctionalized polyorganosiloxane comprising:
  a) end siloxyl units of type $M=(R^6)_3SiO_{1/2}$
  in which the $R^6$ radicals which are identical or different, correspond to an optionally substituted linear or branched $C1-C_6$ alkyl group and/or a substituted or unsubstituted aryl group, and
  b) identical or different siloxyl units of type $D=(R^7)_2SiO_{2/2}$
  in which the $R^7$ radicals correspond to the same definition as $R^6$.

The physical properties of these gels are adjusted according to the use by varying the levels of siloxyl units carrying Si-alkenyl and SiH functional groups and when it is present by varying the percentage by weight of nonfunctionalized polyorganosiloxane, which is well known in the prior art.

To enhance the adhesive properties of the silicone gel, the composition can further comprises a monofunctional polyorganosiloxane carrying a single Si-alkenyl group per molecule as teached by the European patent application EP-1633830-A2.

Further, the composition may also comprise inorganic filler such as reinforcing or bulking fillers. These fillers can be provided in the form of very finely divided products, the mean particle diameter of which is less than 0.1 μm. These fillers include in particular fumed silicas and precipitated silicas; their specific surface is generally greater than 10 $m^2/g$ and generally lies within the range 20-300 $m^2/g$.

These fillers can also be provided in the form of more coarsely divided products, with a mean particle diameter of greater than 0.1 µm. Mention may in particular be made, as examples of such fillers, of ground quartz, calcium carbonate, diatomaceous silicas, calcined clay, titanium oxide of the rutile type, iron, zinc, chromium, zirconium or magnesium oxides, the various forms of alumina (hydrated or nonhydrated), boron nitride, lithopone or barium metaborate; their specific surfaces are generally less than 30 $m^2/g$.

The filler may have a hydrophobic surface, which may be obtained by treating the filler, e.g. with suitable silanes, short chain siloxanes, fatty acids or resinous silicone materials. Suitable materials and processes for rendering the surface of fillers hydrophobic have been described in the literature, and are known to the person skilled in the art. The fillers can also be composed of a mixture of several types of fillers with different particle sizes.

The composition may comprise active agents, which may have any desired activity for the intended purpose, for example medically active agents and the like. Suitable active agents or APIs are radiation stable as hereinbefore defined, preferably are stable under the required radiation levels to achieve terminal sterility of the compositions disclosed herein. These are commonly selected from antimicrobial agents and disinfectants such as silver and derivatives including silver oxide, silver nitrate, silver acetate and silver chloride, biguanides including polyhexamethylene and chlorhexidine glucanate and its acetate salt, active agents such as pharmaceuticals, biocides, growth factors, hemostats and the like, nutrients, pain killers and agents to minimise discomfort and the like and combination materials Antimicrobial agents, biocides and disinfectants may be selected from silver, in particular nano crystalline silver, and derivatives including silver complexes and salts such as ionic silvers, silver zeolite, silver oxide, silver nitrate, silver acetate, silver chloride, silver sulphadiazine), biguanides including polyhexamethylene biguanide and chlorhexidine digluconate and its acetate salt chlorhexidine acetate and diacetate, manuka honey, peroxides (e.g. hydrogen peroxide), iodine (e.g. povidone iodine), sodium hypochlorite, copper, copper complexes; zinc (e.g. zinc oxide, zinc pyrithione), gold, gold complexes; phosphates, amines, amides and sulphonamides (e.g. hexatidine, proflavine, mafenide, nitrofurazone, norfloxacin; antibiotics (e.g. gentamicin, bacitracin, rifampicin; alcohols and acids (e.g. ethanol, phenoxy ethanol, mupirocin); known irradiation stable antimicrobials include Chlorhexidine acetate, silver sulphadiazine (SSD) and nano crystalline silver, these are active components of terminally sterile commercially available products Bactigras™, Allevyn Ag™ and Acticoat™ respectively; nutrients, pain killers and other pain management techniques suitably include analgesics and anasthetics and may be selected from amethocaine, lignocaine, non-steroidal anti-inflammatory drugs);

Heamostats may be selected from Chitin, chitosan, kaolin; Antifibrinolytics such as amino acids, aminocaproic acid, tranexamic acid, aminomethylbenzoic acid; Proteinase inhibitors including aprotinin, alfal antitrypsin, C1-inhibitor, camostat; Vitamin K and other hemostatics including vitamin K, phytomenadione, menadione; Fibrinogen including human fibrinogen; Local hemostatics including absorbable gelatin sponge, oxidized cellulose, tetragalacturonic acid hydroxymethylester, adrenaline, thrombin, collagen, calcium alginate, epinephrine; Blood coagulation factors including coagulation factor IX, II, VII and X in combination, coagulation factor VIII, factor VIII inhibitor bypassing activity, coagulation factor IX, coagulation factor VII, Von Willebrand factor and coagulation factor VIII in combination, coagulation factor XIII, eptacog alfa (activated), nonacog alfa, thrombin. Systemic hemostatics: etamsylate, carbazochrome, batroxobin, romiplostim, eltrombopag; combination materials including superabsorbers, Odour management, Wovens and non wovens, Gellable fibres; Growth factors, Wound debridements—mechanical, autolytic and enzymatic; Resorbable dressings and micro structure to influence cell ingrowth; Cells, tissue (e.g. autologous treatments); Indicators; Dyes and colourants.

The composition may include additional components selected from adjuvants, preservatives, extenders and the like. Adjuvants are preferably selected from fillers, colorants, coloured indicators. Preservatives include propyl gallate.

Preferably a composition comprises, by weight percent:
Part A:
one or more prepolymers (i) (80-99%)
blowing agent (0-10%)
a catalyst (>0-5%)
preservative (0-0.1%)
Part B:
one or more prepolymers (ii) (94-100%)
a foam stabiliser (0-11%)
a catalyst inhibitor (0-0.1%)
preservative (0-0.1%)
diluent or viscosity modifier (0-75%)

Part A:B may be present in a 1:99:99:1, for example 30:70 to 99:1 volume % ratio, respectively with or without added diluent or viscosity modifier. Preferably Part A:Part B is present in 30:70 to 70:30 volume % ratio, more preferably 45:55 to 55:45, such as substantially 50:50. Preferably Parts A and B are of compatible viscosity enabling mixing and substantially complete reaction thereof. Suitably viscosity of Part A:Part B is in the range 6:1-1:8, preferably 5:1-1:5, more preferably substantially 1:1. Compositions of disparate viscosity may be mixed in devices with increased length mixing head for example. The sterilisation of a composition may induce some viscosity increase, and therefore the viscosity ratio is preferably that of the Parts post-sterilisation.

Preferably the composition comprises prepolymers which are relatively short in length compared to that of the intended sterilised prepolymer. Prepolymers undergo chain lengthening during irradiation to a desired final viscosity or density. Preferably the Part A prepolymer(s) having at least one alkenyl unit or moiety per molecule are relatively short in length compared to that of the corresponding sterilised Part A prepolymer(s).

Preferably the respective sterilised Parts are of a viscosity suitable for mixing by hand within a period of up to 1 minute. In a particular advantage Part A and/or Part B may comprise shortened pre-polymers that will increase in molecular weight during sterilisation to give species with the desired properties following sterilisation. More particularly Part A and optionally Part B comprise pre-polymers of chain length determined such that an increase in molecular weight after irradiation sterilisation confers on the prepolymers a desired molecular weight, viscosity, rheology or the like following sterilisation. Most preferably Part A comprises such shortened pre-polymers. Shortening is preferably to a percentage corresponding to the percentage increase in molecular weight and viscosity of the Part during sterilisation. This percentage will vary according to the chemical nature of any given composition. For example for a polydiorganosiloxane composition, shortening of Part A prepolymers is typically to the extent to give a 9-11% reduction in viscosity and shortening of Part B prepolymers is typically to the extent to give a 17-23% reduction in viscosity.

A problem envisaged with dispensing low viscosity compositions in the lower part of the range 5-300 Pa*s is retaining the composition in position at an intended site until cure is complete. Low viscosity compositions tend to flow within or away from an intended site during the initial period of cure, if not contained. WO2004/108175 (Molnlycke Health Care AB) discloses the compounded problem encountered if the composition is affected by movements of the body, pressure or friction. Preferably the composition may have, on initial mixing, a viscosity within the range 10-120 Pa*s, more preferably within the range 20-80 Pa*s. The composition may comprise one or more fillers to confer thixotropic properties thereon. A suitable filler may be fumed silica, for example such as Wacker Chemie, Wacker HDK™. WO2004/108175 discloses Wacker HDK™ as especially effective for this purpose.

Prepolymers (i) and (ii) have cross-linking function, prepolymer (ii) may also cooperate with blowing agent to cause foaming.

More preferably a composition comprises, by part weight, a modification of Cavi-Care composition recited in U.S. Pat. No. 5,153,231 example col 7 the contents of which are incorporated herein by reference, for example in which all of prepolymer i) is moved to Part A:

| Ingredients | Parts by weight |
| --- | --- |
| Part A | |
| Dimethylvinylsilyl endblocked PDMS, viscosity 450 mm$^2$/s, 0.01 mol % vinyl groups | 64 |
| Dimethylvinylsilyl endblocked PDMS, viscosity 9000 mm$^2$/s, 0.002 mol % vinyl groups | 93 |
| Ethanol | 3 |
| Chloroplatinic acid | 4 |
| Propyl gallate | 0.01 |
| Part B | |
| Methyl butynol | 0.05 |
| Trimethylsilyl endblocked polymethylhydrogensiloxane, viscosity 30 mm$^2$/s, 1.5 mol % hydrogen | 16 |
| Polymethylhydrogen-PDMS, viscosity 5 mm$^2$/s, 0.75 mol % hydrogen | 16 |
| Foam stabiliser-hexamethyldisiloxane coated polysilicates treated with the alcohol $F(CF_2)_8CH_2CH_2OH$ | 4 |
| Propyl gallate | 0.01 |
| Silicone oil | Balance (up to 128) |

In a further aspect of the invention there is provided a method of preparing a composition as hereinbefore defined from its composition precursor comprising the steps of:—
combining prepolymers (i), (ii) and catalyst (iii) as hereinbefore defined to form at least one Part A and at least one Part B as hereinbefore defined; and
sealing the Part(s) A and Part(s) B in receptacles with barrier means as hereinbefore defined.

Preferably combining is with additional components, by weight percent as hereinbefore defined In a further aspect of the invention there is provided a method for the sterilisation of the composition comprising irradiating at least one of Part A and Part B, more preferably irradiating with x-ray, gamma and/or e-beam irradiation, most preferably gamma irradiation. Preferably irradiation is in sterilising dose. Preferably Part B or both Parts A and B are irradiated. In the case that only one of Parts A and B is irradiated, the other Part is suitably sterilised by another known or novel means.

Sterilization is regarded as a special process because of the difficulty in verifying by retrospective testing that products which have been through a sterilisation cycle are in fact sterile. Sterilisation controls for medical devices are achieved by a combination of validated sterilisation processes, selection of packaging appropriate to the sterilisation process and the application of quality assurance principles to the control of microbial bioburden on raw materials, intermediates, finished products and the manufacturing environment.

The terminal sterilisation of medical devices and medical products is carried out using gamma irradiation amongst other processes, as defined in BS EN 556—1:2001 Sterilisation of medical devices—Requirements for terminally sterilised devices to be labelled sterile.

Using gamma ray irradiation, short wavelength electromagnetic radiation (photons) are emitted from radioactive substances in the process of nuclear transition. Any radiation source may be used for sterilisation of product, and is preferably the isotope cobalt 60 (60Co). Radiation sterilisation is concerned with the exposure of an item to ionising radiation under defined validated conditions. Using e-beam radiation, continuous or pulsed streams of high energy electrons are emitted.

The radioisotope Cobalt 60 is the energy source for use in gamma irradiation plants and is manufactured specifically for this purpose. The irradiation process takes place in a specially designed cell, constructed of reinforced concrete often up to two meters thick. This design ensures that the radiation is attenuated so that there is no increase in external background levels. Cobalt 60 pellets are sealed inside stainless steel cylinders, referred to as source pencils. These pencils are placed into a metal source rack located within the concrete cell. The source rack can only be in one of two positions: the storage position, which most commonly is within a deep pool of water, or in the raised operating position. During operation, the source rack is surrounded by product circulating on a conveyor system. The energies given out by the decay of Cobalt 60 are insufficient to induce radioactivity in any material, irrespective of the length of exposure to the source. (http://www.synergyhealthplc.com/PDF/Gamma-Processing.pdf)

Electron beam processing is well established as a technology for initiating chemical change at a molecular level in polymers presented as thin sections, for instance, heat shrink tubing and wire and cable insulation. As a result of increased energy available from new generation equipment this technology has established itself as a valuable addition to the range of sterilization processes available for sterilizing medical devices, dressings and pharmaceuticals. Electron beam generation is typically by means of electron accelerators. Electron accelerators can best be described by analogy with a television tube. A heated tungsten filament forms the electron gun, a high voltage placed across the filament draws electrons away from the filament and accelerates them down an evacuated tube. The beam then passes through an oscillating magnetic field which 'scans' it back and forth (analogous to the horizontal scan of a TV tube), so that it emerges from the scan horn through a thin metallic window, usually made from titanium, in a fan-shaped configuration. Products then pass through this curtain of electrons to receive the required dose of irradiation. (http://www.synergyhealthplc.com/PDF/Electron-Beam.pdf)

X-ray irradiation is appropriate for products which are too dense for E-beam. Much more penetrating than E-beam, X-ray is very similar to Gamma rays generated from cobalt with the key difference that X-rays are powered by electricity. High-energy X-rays are high frequency, short-wave length electromagnetic photons. They are emitted when high-energy electrons are stopped by a material that has a high atomic number.

X-rays are generated using high powered beams from electron accelerators. Electron accelerators function in a similar way to large cathode ray tubes in old fashioned TVs. They accelerate electrons from a plasma around a filament using electric fields to the desired energy (or speed). Hence their radiation can be turned on and off. To generate X-rays, the electron accelerator needs to be equipped with an X-ray converter. The X-ray converter is designed to stop the accelerated electrons and is typically a water cooled tungsten or tantalum plate in an appropriate mechanical assembly.

The efficiency for X-ray emission increases with the electron energy and the atomic number of the target material. The X-ray energy spectrum is broad; the maximum photon energy is the same as the kinetic energy of the incident electrons. With X-ray energies of 5 MeV and 7 MeV, product penetration is greater than that provided by gamma rays from an uncollimated cobalt-60 source.

X-rays and gamma rays are both photons. They lose their energy in matter in the same manner and have a good penetration power.

However, their different production processes lead to different emission characteristics:
  The X-ray emission is concentrated along one dimension, which means that a large fraction of X-rays are emitted in the forward direction.
  Gamma ray emission is isotropic. 60Co pencils are usually laid out in a source rack with 2D extension.

Therefore, the X-ray and gamma ray sources are different and the dose rates in the product will also be different. The dose rate is the amount of radiation given per unit of time such as kGy/min.

Simulations based on X-ray and gamma medical device sterilisation facility modelling show a dose rate two times higher for X-rays compared with gamma rays (http://www.emdt.co.uk/article/x-ray-sterilisation-technology-future and http://www.emdt.co.uk/article/x-ray-sterilisation).

The results are determined as the "bioburden" this being the population of viable microorganisms on a product and/or a package. A product is determined "sterile" if free from viable microorganisms.

A sterility assurance level (SAL) is given as the probability of a viable microorganism being present on a product unit after sterilisation. SAL is normally expressed as $10^{-n}$. Requirements for terminally sterilized devices to be labelled "sterile" are defined as a SAL of $10^{-6}$, or in other words that the theoretical probability of there being a viable microorganism present on a device is equal to or less than $1\times10^6$ (BS EN 556—1:2001 Sterilisation of medical devices—Requirements for terminally sterilised devices to be labelled sterile).

A suitable gamma irradiation dose for a composition is in the range 15-42 kGy (Isotron). Different irradiation processes (continuous and passing) are suitable. A reduced dose achieving terminal sterility of more sensitive composition Parts is in the range 15-25 kGy. Preferably a dose is in the range 15 kGy+/−10% or 15-20 kGy.

e-Beam irradiation is suitable for sterilising compositions of low receptacle wall density and low volume. A suitable dose is delivered by 10 MeV electron beam (Isotron).

The composition may be terminally sterile, i.e sterilised in its (primary) packaging, or otherwise, eg aseptically filled.

In a further aspect of the invention there is provided a method of preparing an elastomer comprising combining the at least one Part(s) A and at least one Part(s) B of a composition as hereinbefore defined with curing or crosslinking thereof.

The method may be a method of preparing a porous foam, adhesive or sealant comprising combining the at least one Part(s) A and at least one Part(s) B of a foamable and/or adhesive or sealant composition as hereinbefore defined with curing or cross linking thereof.

Preferably the method is carried out in a sterile field.

In a further aspect of the invention there is provided an elastomer comprising a cured or crosslinked composition as hereinbefore defined.

The elastomer is suitably obtained by combining the at least one Part(s) A and at least one Part(s) B of a composition as hereinbefore defined with curing or crosslinking thereof.

The elastomer may be a porous foam, adhesive or sealant comprising a cured or crosslinked foamable and/or adhesive or sealant composition as hereinbefore defined.

The porous foam, adhesive or sealant elastomer may be obtained by combining the at least one Part(s) A and at least one Part(s) B of a foamable and/or adhesive or sealant composition as hereinbefore defined with curing or cross linking thereof.

Preferably the elastomer is terminally sterile. By "elastomer" is meant the resulting end-product obtained after combining or mixing the at least one Part A and at least one Part B to form a mixture, with curing or crosslinking thereof. Curing or crosslinking is suitably initiated by subjecting to low (less than room temperature (around 20 C), ambient (room temperature) or high temperature (greater than room temperature up to 190 C).

In a further aspect of the invention there is provided the medical or non-medical, dental or non-dental use of a composition or elastomer as hereinbefore defined. Such use includes use as dyes; preservatives; gels; foams; aerosols; pharmaceuticals; adhesives; encapsulants; hair/skin care; cosmetic use; dental use; release coatings; coatings; adhesives and sealants; wound care; skin care including scar reduction; cavity care; medical device encapsulation such as electronic device encapsulation for biomedical applications; mould making; orthopaedics; drug delivery systems including antimicrobial systems; haemostatic and pharmaceutical systems; nutrition including manufacture of foodstuffs; aerospace, marine and submarine applications; ecologically sensitive applications; confined or isolated organisms, or their habitats, or confined or isolated medium or atmosphere such as those having low immunity; sterile, clean or aseptic applications; germination or propagation of living matter such as plants or organisms; including manufacture and repair of equipment, apparatus or components for any of the above and in particular aerospace, submarine sterile, clean or aseptic, germination or propagation.

A medical use of particular advantage is as a foamable composition as hereinbefore defined. A foamable composition is particularly suited for use in wound therapy, more particularly for use as a wound filler or wound packing material or cavity foam dressing, most particularly in NPWT. The foamable composition is of particular advantage in that it may be used in a sterile field or environment. It is in this field, working on very severe wounds, that the advantages of a dispensable shapable foam are most relevant, and yet a non-sterile composition can not be used.

Accordingly embodiments disclosed herein enable for the first time the use of a curable foam composition in a sterile field.

The foamable composition for use in wound care or wound therapy is suitable for providing a porous cured three dimensional resiliently deformable body. This is of particular advantage in providing support for the wound whilst being compressible as the wound heals and closes.

Preferably the foamable composition provides an open-pore cured three dimensional body. In the case of a composition suited for NPWT, the open pore system allows the development of a negative pressure at the wound, transmitted through the open-pore foamed body. Wound fluids may be evacuated through the foamed body.

In foam based NPWT the wound cavity is filled or covered with a porous foam packing material and covered over and sealed with flexible sheet (a drape) that is fairly impermeable to fluids. In gauze based NPWT a corresponding procedure is followed but using gauze packing material in place of porous foam packing material. In combination dressing or preformed dressing based NPWT either procedure may be followed if gauze or foam are to be used. A vacuum line is inserted under or through the drape into the wound site and its distal end is connected to a vacuum source (commonly a pump). The wound cavity, enclosed by the drape and tissue, contracts under the force of atmospheric pressure and compresses the packing material visibly. Gross tissue movement ceases after a few tens of seconds and fluid flow from the wound (withdrawn from the tissue) ensues. The fluid is transmitted through the packing material and up the vacuum line to a collection receptacle positioned between the distal end of the vacuum line and the vacuum source. The wound packing material mechanically supports the tissue to which it is applied, and also allows the free flow of fluids away from the site when a vacuum is applied, even when compressed.

Porosity is a function of number of pores and their size. It can be conveniently measured as a function of volume increase. The foamable composition suitably delivers a foam having a volume increase compared to the composition in the range from 3 to 10. Volume increase may be regulated by choice and amount of foaming agent, but is also a function of the polymer. In a particular advantage the compositions, and in particular the polydiorganosiloxane compositions, deliver porosity which is eminently suitable for wound care applications. Preferably, the body is of very high free internal volume, e.g. 70%-90% as hereinbefore defined.

Generally, the size of the pores affects the transmission of negative pressure. Therefore, the smaller the pores, the smaller the negative pressure which can be established and the shorter its duration as the foam is progressively compressed by surrounding tissue growth. However the larger the pore size the lower the tensile strength, and the lower the support which the foam is able to deliver.

The composition suitably delivers a foamed cured material having resilience and tensile strength capable of withstanding negative pressure of broadly −40 to −200 mmHg such as 80-120 mmHg below ambient atmospheric pressure without causing the foam to collapse. In a preferred embodiment the pores are resilient to tissue contraction, and do not collapse under contraction, whereby negative pressure may be maintained.

Preferably a foamable composition is adapted to deliver a foam which is open at its interfaces with moist or wet surfaces, more preferably is a polydiorganosiloxane composition. This creates the ideal material for generating a negative pressure at a wound surface whilst maintaining open communication with the wound itself.

The polydiorganosiloxane composition is adapted to deliver negative pressure selectively to moist wound surfaces for example via an aperture or valve which can be readily inserted directly at its sealed face remote from the wound surface or indirectly via a vacuum connection tube connecting to such sealed face.

In a preferred embodiment the pores are resilient to tissue contraction, and do not collapse under contraction, whereby negative pressure may be maintained. The composition suitably delivers a foamed cured material having resilience and tensile strength capable of withstanding negative pressure of more than—150 mmHg, preferably 60-120 mmHg such as 60-100 mmHg below ambient atmospheric pressure, or 80-120 mmHg below ambient atmospheric pressure without causing the foam to collapse.

Preferably a foamable composition is adapted to deliver a foam which is open at its interfaces with moist or wet surfaces, more preferably is a silicone composition. This creates the ideal material for generating a negative pressure at a wound surface whilst maintaining open communication with the wound itself. In a further advantage the composition is suitable for providing a cured porous three dimensional body of desired shape.

The polydiorganosiloxane composition is adapted to deliver negative pressure selectively to moist wound surfaces, for example via an aperture or valve which can be readily inserted directly at its sealed face remote from the wound surface or indirectly via a vacuum connection line connecting to such sealed face.

It will be appreciated that throughout this specification reference is often made to a wound. In this sense it is to be understood that the term wound is to be broadly construed and encompasses open and closed wounds in which skin is torn, cut or punctured or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, trauma and venous ulcers or the like. Certain embodiments of the present invention are not restricted to use with wounds as will be discussed in more detail hereinbelow. Use as a wound filling material, preferably a negative pressure wound therapy wound filling material as hereinbefore defined includes use on wounds selected from chronic, acute, traumatic, sub-acute and dehisced wounds, ulcers (such as pressure or diabetic), partial-thickness burns and flaps and grafts. These include open, moist, granulating wounds, preferably surgical wounds such as those resulting from excision of ulcers, cancerous tissue such as perianal and perineal wounds and the like. For optimum healing of such wounds, the wound should be prevented from closing in on itself and allowing fluids to accumulate, whilst at the same time allowing the tissue around the wound to progressively contract, and the wound to shrink. Wound filling materials in NPWT therefore function as a type of "stent", supporting the wound and holding it open.

Further medical or non medical uses for which the composition is particularly advantageous include use as an adhesive or sealant composition as hereinbefore defined. An adhesive or sealant composition is particularly suited for use in clean, aseptic or sterile applications, more particularly as an adhesive or sealant for clean aseptic storage or packaging of items such as medicaments, particularly packaging medicaments within a medical device, or nutritional items and the like, or in the repair and/or maintenance and/or manufacture of sterile, aseptic or clean devices or machinery.

Preferably the composition for use as an adhesive or sealant in sterile, clean or aseptic conditions is packaged within further barrier means as hereinbefore defined. Further barrier means provide a barrier to infection. The composition is therefore a double wrapped item, this allows for the removal of the first layer of sterile sealed packaging to reveal receptacles or supports such as cartridges for or incorporated in a syringe, adhesive strips and the like, which are completely sterile inside and out, facilitating entry into a sterile environment. The composition omitting a further barrier means would comprise a non-sterile external surface of receptacles or supports and associated barrier means. As it is not possible to sterilise the composition using standard conditions for medical apparatus as hereinbefore described, it would not be possible to take such a composition into a sterile field.

The adhesive or sealant composition is suitable for introducing into a clean or aseptic area and dispensing or releasing into contact with an item to be adhered or sealed. Optionally a closure means is applied thereto. For example a bead of sealant may be dispensed around the rim of a sterile bottle prior to application of a closure means, or to any surface which it is desired to seal. A closure means or other opposing or adjacent surface is suitably applied with application of light pressure thereby ensuring that a seal is produced between the rim and the lid or other opposing or adjacent surfaces. In this way a universal sterile sealant is made available to the surgeon or clinician, lab technician, food manufacturer or mechanic. The sealant may be provided in a bagged dual syringe applicator and dispensed though a static mixer at the point of use. In this way a sterile dispenser and sealant may be conveniently provided for the user.

Certain sealant composition may be useful for example in sealing medical dressings, is useful for example in restraining egress of wound exudate or ingress of infection, or providing a vacuum seal for NPWT application; or as an insitu sterile lid sealant for laboratory vials and other vessels (e.g. Petri dish lids, sample storage pots, bijou bottles, culture bottles, demijohns and dewars) under clean or aseptic techniques; or in the aseptic manufacture of packaged nutritional items such as for example foodstuffs including milk, fruit juice, egg; or in the repair and/or maintenance and/or manufacture of sterile, aseptic or clean devices or machinery and the like.

A sealant for medical dressings may be applied in any known or novel manner. WO 00/74738 (Guyuron) discloses use of silicone based RTV-2 compositions to seal wounds i.a to minimise potential infections. The sealant of the invention may suitably therefore be used by casting on top of the wound and surrounding skin and allowing to cure.

WO2004/108175 (Molnlycke Health Care AB) discloses use of silicone based RTV-2 compositions to disintegrating skin or skin around wounds i.a to minimise potential infections and protect against harmful effects of wound exudate. The sealant is used by applying to skin about a wound, or to disintegrating skin, applying an adhesive or non-adhesive dressing over the wound and in contact with the sealant and allowing to cure, or by applying to an adhesive or non-adhesive dressing, applying the dressing to a wound and allowing to cure. In either case the dressing is sealed to the skin about the wound. The composition presents an admirable improvement on these methods by providing the surgeon, clinician or patient with a sterile sealant for use in these known manners or modifications thereof.

Foodstuffs may be sealed within a container e.g. Tetra Pak as hereinbefore described. In this way the sealant may be provided in bulk for industrial scale automated mixing and dispensing (e.g. using robotic dispensing systems as supplied by Rampf Dosiertechnik GMBH) in aseptic conditions. Sterile bagged cartridges of the 2 components may be manufactured for insertion in the dispensing machine. In this way sterile cartridges of the 2 components may be provided for delivery into the aseptic manufacturing area and insertion into the dispensing machine.

In the repair and/or maintenance of machinery, particularly envisioned is the replacement of gaskets. Here the sealant may be applied to a flange area or sealing surface as a bead prior to the bringing together of the components to form a seal. This reduces the need to sterilise individual gaskets prior to introduction to the aseptic environment and may reduce the need for multiple gaskets to be purchased or manufactured. In the aseptic manufacture of devices or machinery, particularly envisioned is the manufacture of space craft, marine or submarine craft, or components thereof in order to meet planetary protection requirements. Here the sealant composition may be dispensed to create an insitu gasket as hereinbefore defined. Alternatively the foamable composition may be dispensed as anti vibration material or insulation for heat or electrical purposes. The sealant may be provided in a bagged dual syringe applicator and dispensed though a static mixer at the point of use. In this way a sterile dispenser and sealant may be conveniently provided for the user. Alternatively sterile bagged receptacles such as cartridges of the composition Parts may be provided for delivery into an aseptic manufacturing area and insertion into a dispensing machine.

In a further aspect there is provided a wound dressing comprising the foamable or foamed composition, adhesive or sealant or composition thereof as hereinbefore defined.

In a further aspect there is provided a method for dispensing or releasing, and curing a composition as hereinbefore defined, comprising dispensing into a desired location or aperture at curing temperature for curing time.

The composition may be manually mixed and dispensed. Alternatively any form of dispensing device may be employed.

In a further aspect of the invention there is therefore provided a composition dispensing device comprising a terminally sterile composition as hereinbefore defined. Preferably the device is a NPWT device. Suitably a device comprises a mixing head having means to receive 2 or more cartridges comprising Parts A and B. Cartridges are adapted to locate and lock in place in the device. A suitable device for NPWT is a double barrelled syringe suitable for loading with 40 g of pre-polymers and fitted with a mixing head.

In a further aspect there is provided a method of therapy comprising dispensing a sterile composition as hereinbefore defined, preferably a terminally sterile composition, to the site of a wound.

In a further aspect there is provided a method of therapy as hereinbefore defined which is a method of negative pressure wound therapy comprising dispensing a terminally sterile composition as hereinbefore defined directly or indirectly into a wound and allowing to foam and cure, sealing the wound including the foamed cured composition and optionally including a negative pressure connection means, and applying negative pressure to the wound.

The composition may be dispensed directly into an open wound cavity and covered or dispensed into a covered cavity via an aperture in the cover or dispensed into a mould and inserted into a wound cavity. An open-pore surface or recess of surface is generated which may be connected directly or indirectly to a negative pressure source.

Currently available wound fillers require removal and cleansing or changing on a regular basis, typically every 8, 12 or 24 hours, with the maximum recommended period for a dressing to remain in place being 48 hours in the case for example of foam, although up to 72 hours for black foam, and 72 hours in the case of gauze. After longer periods tissue in-growth may occur. In the case of foam the washed dressing may be reused for up to a week, but as wound healing progresses successively smaller fillers should be produced.

In a particular advantage, the composition may be dispensed into a prepared wound in a sterile field and may remain in situ without the need to cleanse and replace because the shaping process is simplified and highly accurate, rather the used filler is discarded and a new filler is simply dipensed. The degree of tissue contraction which has taken place may be determined by monitoring a reduction in the negative pressure being delivered or by a decrease in the resilient deformation of the cured composition, and if sufficient contraction is observed, the cured composition may be removed and new composition dispensed into the wound for continued therapy. The foamable curable composition preferably has a pore structure which is capable of being compressed under moderate pressures, as tissue contracts, without pore collapse.

The composition may be manually mixed and dispensed. Alternatively any form of dispensing device may be employed. In a further aspect of the invention there is therefore provided a composition dispensing device comprising a terminally sterile composition as hereinbefore defined. Preferably the device is a NPWT device. Suitably a device comprises a mixing head having means to receive 2 or more cartridges comprising Parts A and B. Cartridges are adapted to locate and lock in place in the device. A suitable device for NPWT is a 40 g mixing head In a further aspect there is provided a method for treating a wound site, comprising:
  dispensing a terminally sterile composition around at least a portion of the wound site, wherein the composition comprises a sealant capable of making a substantially fluid-tight seal;
  covering the wound site with a substantially fluid-tight drape, the drape contacting at least a portion of the dispensed terminally sterile composition and forming a fluid-tight seal over the wound; and
applying negative pressure to the wound site using a source of negative pressure connected to the wound site.

Preferably the composition comprises a first part and a second part.

Preferably the method further comprises curing the composition during or after covering the wound site.

Preferably the method further comprises placing a filler such as foam, gauze or the like into the wound site.

The drape suitably comprises an aperture so as to connect the source of negative pressure. The aperture may be positioned centrally, to one side or at the perimeter of the drape. The method may further comprise creating at least one aperture into or under the drape so as to connect the source of negative pressure.

Preferably the terminally sterile composition is sterilized prior to dispensing by exposing the composition to radiation in terminally sterilising dose.

Preferably the terminally sterile foamable composition is a composition as hereinbefore defined.

In a further aspect of the invention there is provided a method for treating a wound site, comprising:
  applying a dressing to a wound site
  releasing a first part A of a terminally sterile composition from a support around at least a portion of the wound site and exposing the said part,
  exposing a second part B of a terminally sterile composition supported on a fluid-tight drape
  covering the wound site with the drape, thereby contacting and adhering the exposed first and second parts and adhering the drape around the wound site; and
applying negative pressure to the wound site using a source of negative pressure connected to the wound site.

It is envisaged that the negative pressure range for certain embodiments of the present invention may be between about −20 mmHg and −200 mmHg (note that these pressures are relative to normal ambient atmospheric pressure thus, −200 mmHg would be about 560 mmHg in practical terms). Aptly the pressure range may be between about −40 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

It will be appreciated that according to certain embodiments of the present invention the pressure provided may be modulated over a period of time according to one or more desired and predefined pressure profiles. For example such a profile may include modulating the negative pressure between two predetermined negative pressures P1 and P2 such that pressure is held substantially constant at P1 for a pre-determined time period T1 and then adjusted by suitable means such as varying pump work or restricting fluid flow or the like, to a new predetermined pressure P2 where the pressure may be held substantially constant for a further predetermined time period T2. Two, three or four or more predetermined pressure values and respective time periods may be optionally utilised. Aptly more complex amplitude/frequency wave forms of pressure flow profiles may also be provided eg sinusoidal, sore tooth, systolic-diastolic or the like etc.

In a further aspect of the invention there is provided a wound dressing comprising the foamed composition as hereinbefore defined. Preferably the wound dressing is a NPWT wound dressing.

In a further aspect of the invention there is provided a NPWT kit comprising a fluid-tight wound dressing, a dispensable or releasable terminally sterile curable composition and attachment means for a vacuum pump to supply a negative pressure to the dressing. Preferably the terminally sterile curable composition is a composition of the invention as hereinefore defined.

BRIEF DESCRIPTION OF THE DRAWINGS

Embodiments of the invention will now be illustrated in non limiting manner with reference to the Figures in which
FIGS. 1 and 2 illustrate a NPWT foam filler wound dressing;
FIGS. 3 and 7, 8, 9 and 10 illustrate the use and application of a dispensible sterile foam filler wound dressing onto a patient;
FIGS. 4, 5 and 6 illustrate the a kit including a sealant composition and wound dressing;

FIGS. 11 to 15 illustrate the use and application of an embodiment of a wound cover kit, apparatus and sealant onto a patient.

DETAILED DESCRIPTION OF SOME EXEMPLIFYING EMBODIMENTS

Referring now to FIG. 1, in conventional foam based NPWT the wound cavity (1) is filled or covered with a porous foam packing material (2), that may need to be cut to shape (2× shown as a) and covered over and sealed with an adhesive flexible sheet (a drape, 3) that is fairly impermeable to fluids.

Figure 2B:
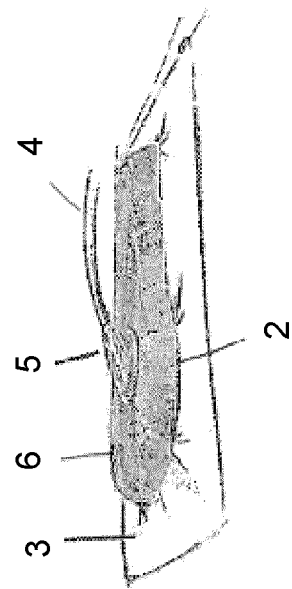
Figure 2A:
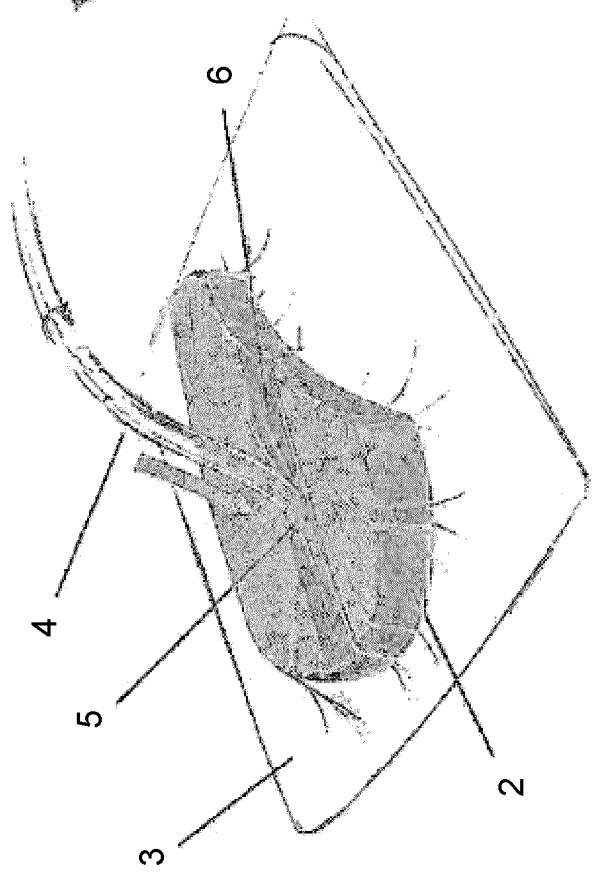

Referring to FIG. 2, a vacuum line (4) is inserted (5) under or through the drape (3) into the wound site (1), in various embodiments this is received in a aperture or groove in the foam (6), or wrapped in gauze. The distal end (not shown) of vacuum line (4) is connected to a vacuum source (commonly a pump, not shown). The wound cavity, enclosed by the drape and tissue, contracts under the force of atmospheric pressure and compresses the packing material or dressing visibly. The system is however prone to vacuum leakage.

In FIG. 3A, a sterile foamable composition is shown (10) being dispensed from syringe (11) into wound site (1). In FIG. 3B, the composition cures once dispensed to form a foamed block (12) contacting the wound bed (1). In FIG. 3C, a drape (3) is placed thereover and sealed in place in conventional manner. Vacuum line (4) is inserted (5) through the drape (3) in conventional manner whereupon vacuum may be initiated via vacuum line (4). The wound cavity behaves in corresponding manner as described in relation to FIG. 2. This system improves the fit of the foam filler, and reduces the stresses placed on the adhesive sealing drape.

Figure 5:
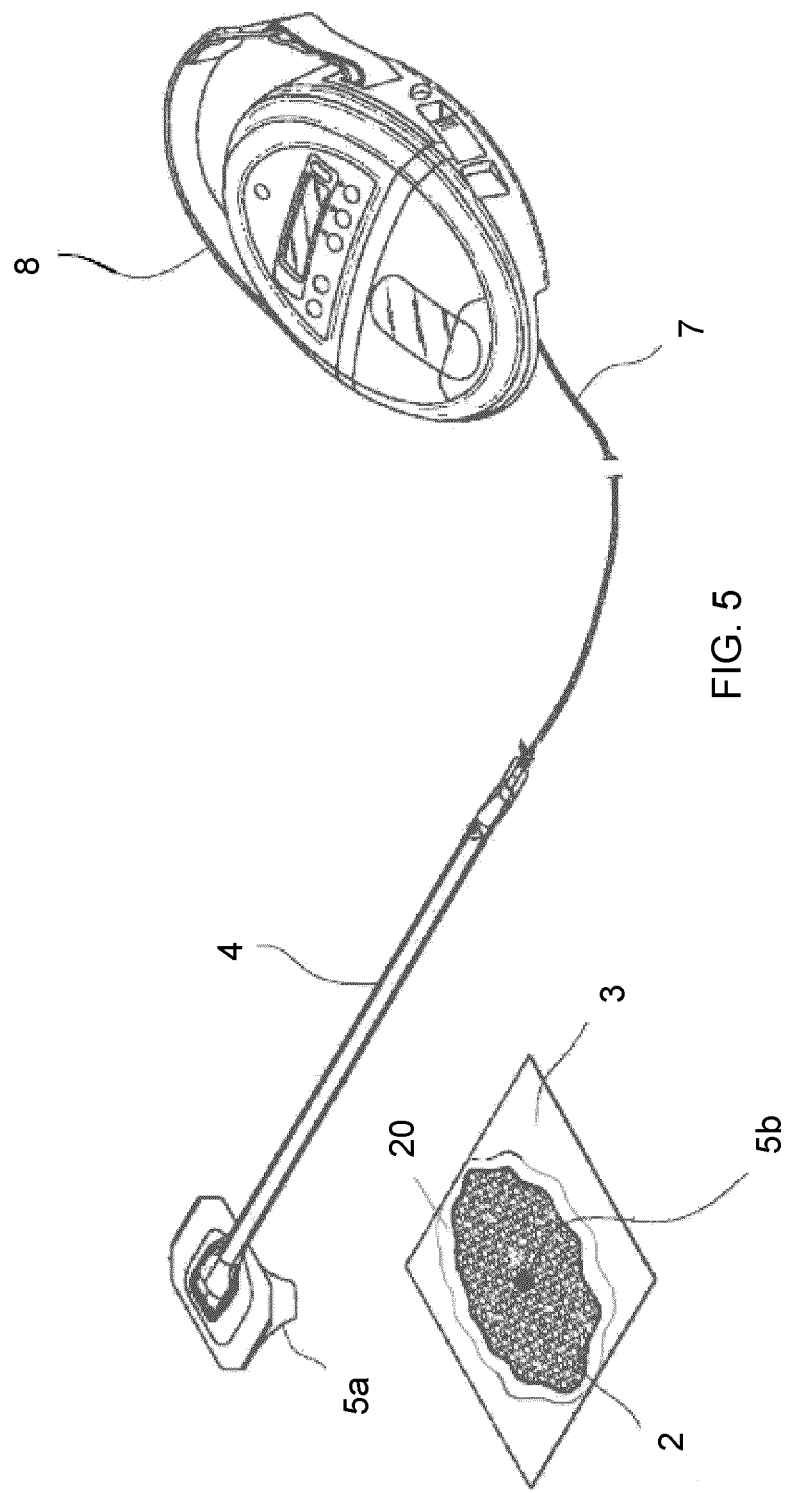

FIG. 4A illustrates a composition for use as a NPWT sealant. The sealant (20) is used by applying to skin about or around a wound site (1), or to disintegrating skin. Adhesive or non-adhesive drape (3) is applied, with optional dressing (not shown) over the wound (1) and in contact with the sealant (20) and the sealant is allowed to cure in contact with the drape. Vacuum line (4) is inserted through an aperture (5) in the drape (3) in conventional manner whereupon vacuum may be initiated via vacuum line (4). The sealant improves the quality of the negative pressure transmitted to the wound bed. FIG. 5 shows a variant of FIG. 4, in which the pump (8) is removably connected (5a) through aperture (5b) in the drape (3).

Figure 6:
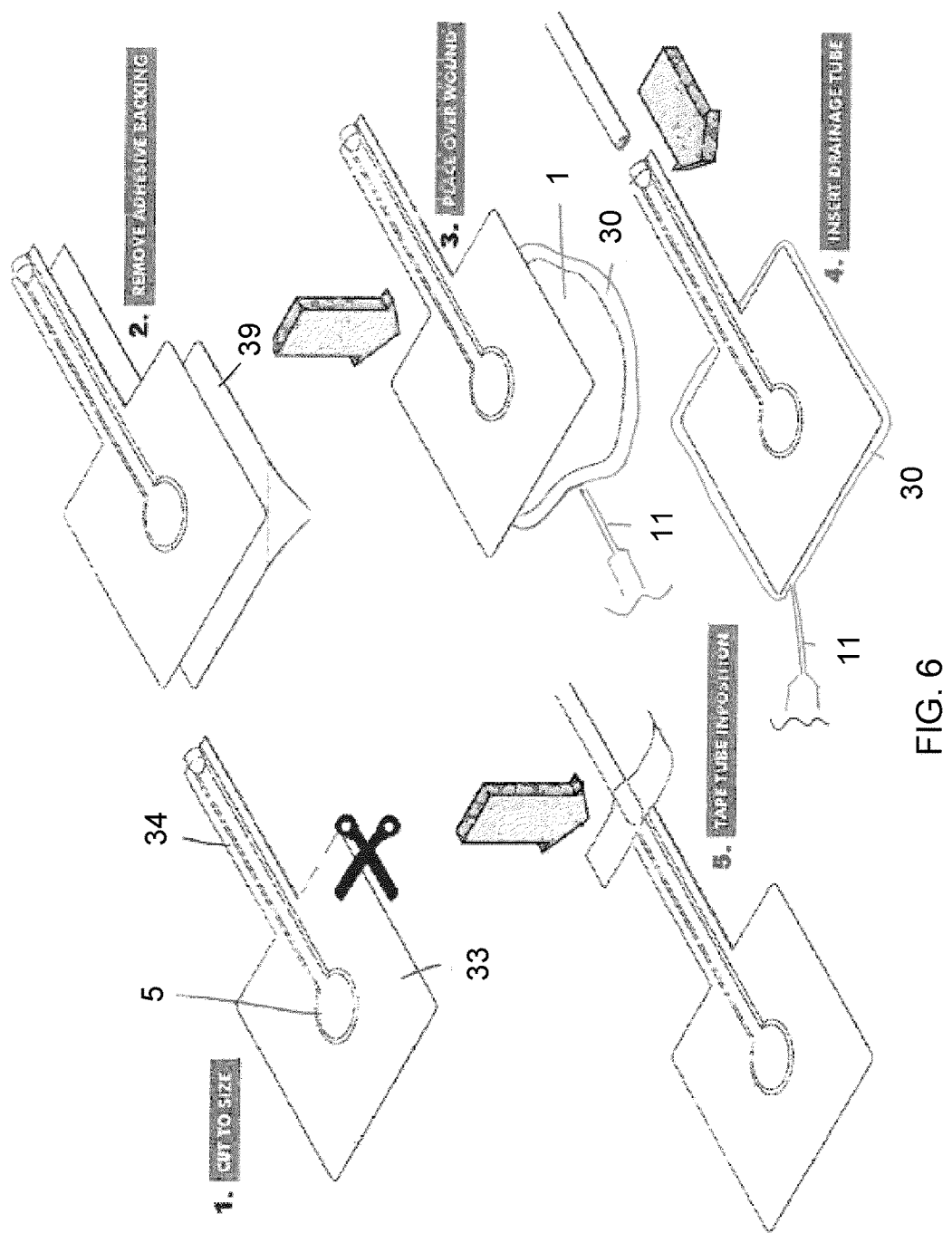
Figure 7:
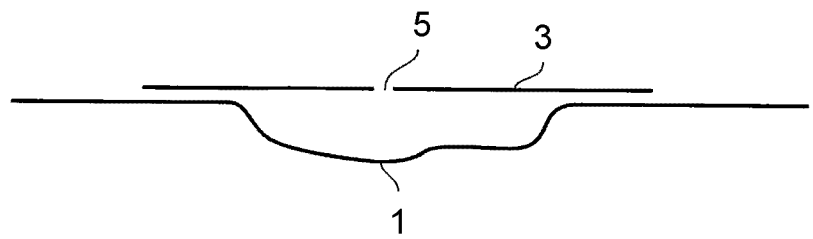
Figure 8:
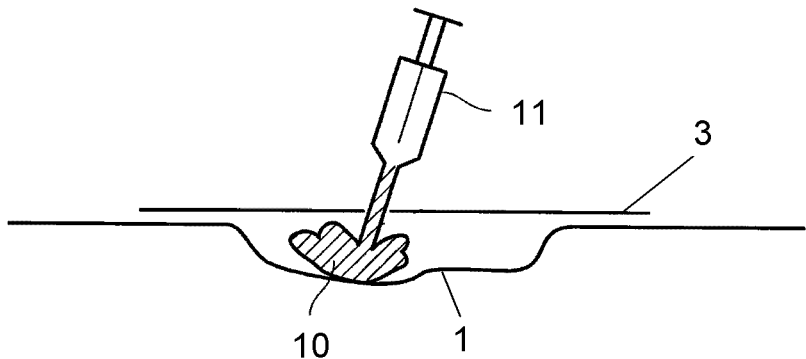
Figure 9:
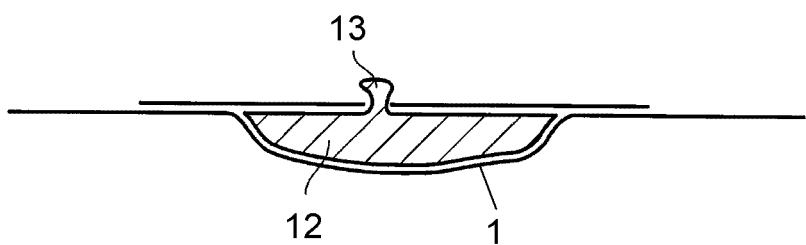

FIG. 6 shows a further variant in which preformed drape (33 incorporating integral vacuum line sheath (34) and aperture (5) is positioned over sealant (30) applied via syringe (11). In this case the drape (33) incorporates an adhesive backing (39), and sealant is therefore either dispensed about the wound in conventional manner as shown in step 3, or sealant (33) is dispensed to the edges of the adhered drape (33) as shown in step 4.

Figure 10:
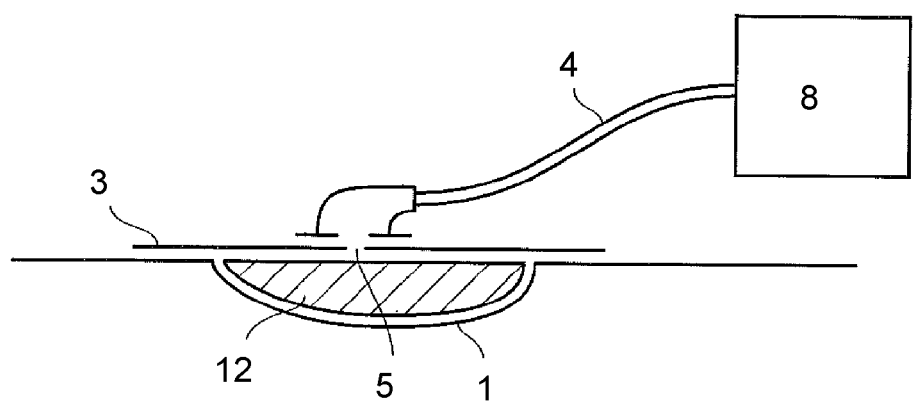
Figure 13B:
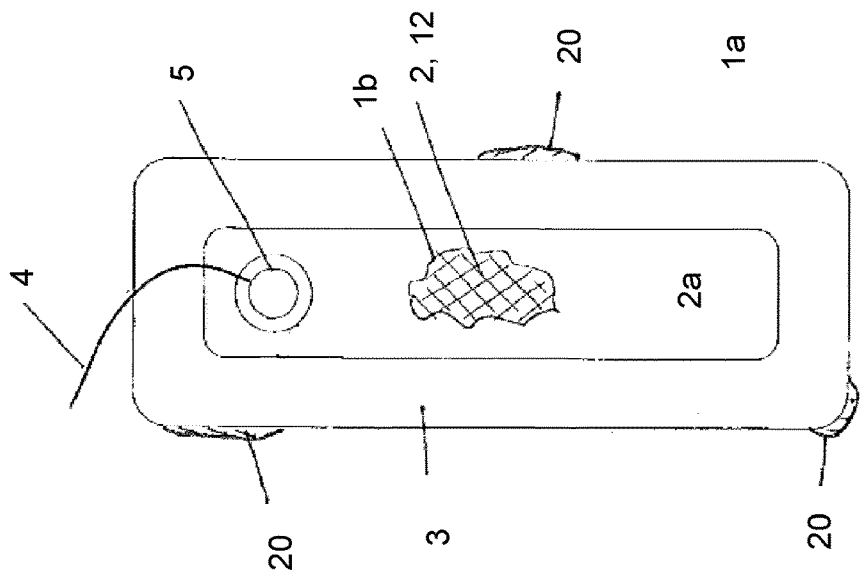
Figure 13A:
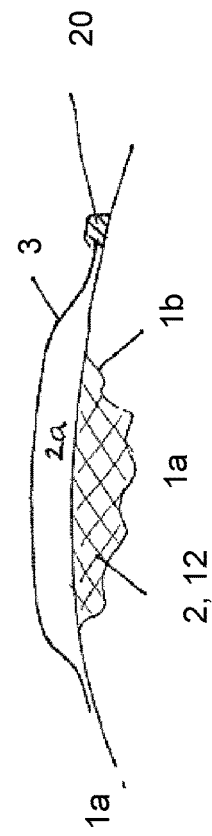

FIGS. 7 to 10 show a further variant to FIGS. 3A to 3C, in which the drape (3) is placed over the wound site (1) before composition (10) is dispensed from syringe (11) through aperture (5). The composition foams and cures to form a foamed block (12) including button (13) projecting through aperture (5). Button (13) is broken off to provide an aperture into the foam body. FIG. 10 shows vacuum line (4) coupled to aperture (5) and connected to vacuum pump (8) in conventional manner.

Figure 15B:
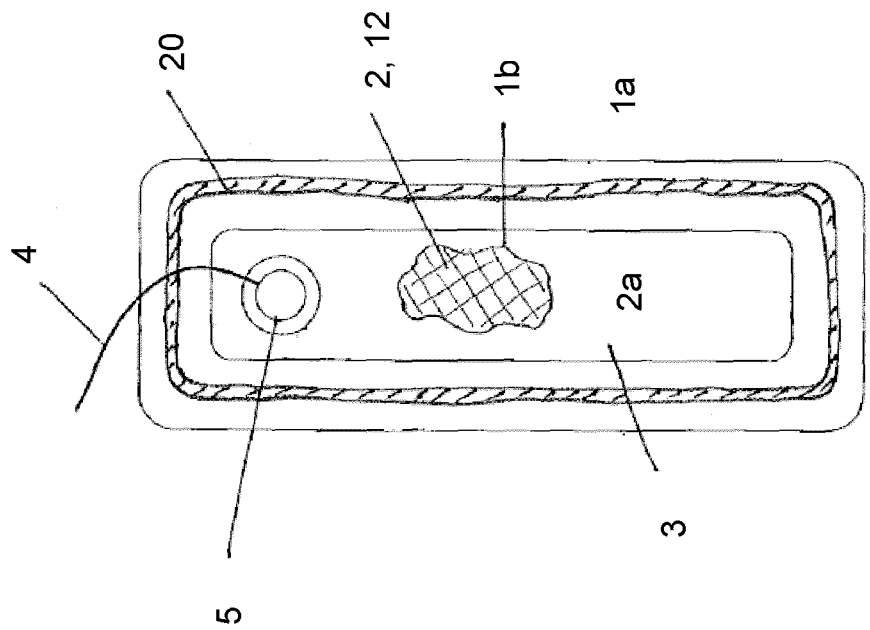
Figure 15A:
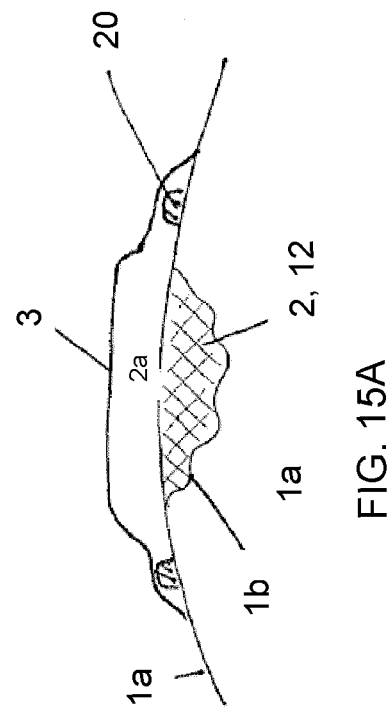

FIGS. 11 to 15 show variants to FIGS. 4a, 5 and 6, relating to dispensing sealant 20 to seal combination dressings/drapes (2a, 3) including integral port (5) for vacuum line (4). For these combination dressings (2a, 3) it is necessary to dispense the sealant (20) to the region of skin (1a) which will underly the perimeter portion of the drape (3) surrounding the dressing portion (2a), as shown in FIG. 15. In the case that it is difficult to prejudge where this perimeter portion will contact the skin (1a), dispensing about the edge of the combination dressing (2a, 3) is advantageous, as in FIGS. 11 and 12. Alternatively sealant (20) may be dispensed at the edge of the drape at positions where leakages can be observed or are suspected. Alternatively sealant (20) may be dispensed directly to the combination dressing, also illustrated in FIG. 15, as a gasket (2), and the dressing then applied over the wound. In all cases, adhesive tape strips (3a) can be overlaid to ensure both adhesion and seal are satisfactory. In all cases, curing, sealing and operation of the vacuum are as previously described.

The invention may be carried into practice in various ways, and embodiments thereof will now be described by way of example only.

COMPARATIVE EXAMPLE

EXAMPLE CE1

Preparation of Composition

RTV-2 polydimethylsiloxane composition Cavi-Care is a commercially available (Smith & Nephew) RTV-2 Pt catalysed foamable silicone elastomer having 30-105 seconds rise time, packaged as Parts A and B in foil pouches formed from aluminium foil laminated to either face with PE.

Rhodorsil RT Foam 3240 A/B (Bluestar Silicones) is a RTV-2 Pt catalysed foamable silicone elastomer having 7.5 minutes rise time.

Sterilisation

The compositions were subjected to gamma irradiation using a Co source irradiation and e-beam irradiation at 10 MeV, at 10, 15, 20 and 25 kGy.

After sterilisation the following were determined and compared with unsterilised polymer:

Viscosity

In each case, the composition Part B formed a solid elastomer (gamma) and underwent an increase in viscosity (e-beam). The composition Part A underwent an increase in viscosity with either radiation means, with gamma at 25-42 kGy, increase in viscosity was 230% (Cavi-Care) or 850% (Rhodorsil).

Curing

Gamma irradiated Cavi-Care and Rhodorsil Part B could not be subsequently reacted to provide an acceptable foamed cured product. Irradiated Rhodorsil Part A cured with non-irradiated Part B gave an unacceptsbly long cure time, in the case of gamma and e-beam.

Foam Density and Compressibility not tested.

Sterility testing

This was not tested as the sterilised composition were not curable.

The gamma irradiation dose is expected to have achieved sterilisation.

EXAMPLE 1

A Two Part Composition and a Method for its Preparation will Hereinafter be Described The viscosities of the following examples correspond to a dynamic viscosity quantity which was measured, in a way known per se, at 25° C. The viscosities were measured using a Brookfield viscosimeter according to the instructions of the AFNOR NFT 76 106 standard of May 1982. These viscosities correspond to a "newtonian" dynamic viscosity quantity at 25° C., that is to say the dynamic viscosity which is measured, in a way known per se, at a shear rate gradient which is sufficiently low for the viscosity measured to be independent of the rate gradient.

Some two-component compositions comprising parts P1 and P2, the composition of which are described in Table 1, were prepared:

1) Components in Part a of the Tested Compositions:
M=$(CH_3)_3SiO_{1/2}$, $M^{Vi}$=$(CH_3)_2ViSiO_{1/2}$ or $(CH_2$=$CH-)(CH_3)_2SiO_{1/2}$, $D^{Vi}$=$(CH_3)(Vi)SiO_{2/2}$ or $(CH_2$=$CH-)(CH_3)SiO_{2/2}$ and Q=$SiO_{4/2}$ a: Vinylated polyorganosiloxane resin comprising M, $D^{Vi}$ and Q siloxyl groups (also named as <<$MD^{Vi}Q$>> resin) with:

b1: polydimethylsiloxane blocked at each of the chain ends by a $M^{Vi}$ unit and having a viscosity of 3500 mPa·s at 25° C.

b2: polydimethylsiloxane blocked at each of the chain ends by a $M^{Vi}$ unit and having a viscosity of 100 000 mPa·s at 25° C.

b3: polydimethylsiloxane blocked at each of the chain ends by a $M^{Vi}$ unit and having a viscosity of 1 500 mPa·s at 25° C.

b4: polydimethylsiloxane blocked at each of the chain ends by a $M^{Vi}$ unit and having a viscosity of 230 mPa·s at 25° C.

c1: diatomeceous earth, sold under the trade name CELITE-SF©.

c2: Fumed treated silica having a low specific surface of 30 $m^2/g$ (BET), sold under the trade name AEROSIL® RY50 d: Hexanol.

e: Karstedt platinum catalyst.

f1: polydimethylsiloxane blocked at each of the chain ends by a M unit and having a viscosity of 1000 mPa·s at 25° C.

g: poly(vinylmethyl)(dimethyl)siloxane oil having a content of $D^{Vi}$ unit of 2% by weight and a content of $M^{Vi}$ unit of 0.4% by weight.

2) Components in Part B of the Tested Compositions:

a: Vinylated polyorganosiloxane resin comprising M, $D^{Vi}$ and Q siloxyl groups (also named as <<$MD^{Vi}Q$>> resin).

b1: polydimethylsiloxane blocked at each of the chain ends by a $(CH_3)_2ViSiO_{1/2}$ unit and having a viscosity of 3500 mPa·s at 25° C.

b2: polydimethylsiloxane blocked at each of the chain ends by a $(CH_3)_2ViSiO_{1/2}$ unit and having a viscosity of 100 000 mPa·s at 25° C.

f1: polydimethylsiloxane blocked at each of the chain ends by a $(CH_3)_3SiO_{1/2}$ unit and having a viscosity of 1000 mPa·s at 25° C.

f2: polydimethylsiloxane blocked at each of the chain ends by a $(CH_3)_3SiO_{1/2}$ unit and having a viscosity of 100 000 mPa·s at 25° C.

i: polydimethylsiloxane oil blocked at each of the chain ends by a $(CH_3)_2HSiO_{0.5}$ unit h: polymethylhydrogenosiloxane oil blocked at each of the chain ends by a $(CH_3)_3SiO_{0.5}$ unit.

j: solution comprising 1% of ethynylcyclohexanol in a polydimethylsiloxane oil blocked at each of the chain ends by $(CH_3)_2ViSiO_{1/2}$ units, having a viscosity of 600 mPa·s at 25° C.

The compositions tested are described in Table 1 below:

TABLE 1

| COMPOSITIONS: Parts by weight | | | | |
|---|---|---|---|---|
| | Ex. 1 | Ex. 2 | Ex. 3 | Ex. 4 |
| Ingredients Part A | | | | |
| a | 20.39 | 15.09 | 19.13 | 20.17 |
| b1 | 61.17 | 45.26 | 57.39 | 60.50 |
| b2 | 12.51 | | | 12.49 |
| b3 | | 35.19 | | |
| b4 | | | 15.00 | |
| c1 | | | | |
| c2 | 0.94 | 1.26 | 1.25 | 1.87 |
| d | 3.63 | 3.11 | 3.62 | 3.62 |
| e | 0.11 | 0.10 | 0.11 | 0.11 |
| f1 | | | | |
| g | 1.25 | | 3.50 | 1.25 |
| Ingredients Part B (C*) | | | | |
| a | | | | |
| b1 | | | | |
| b2 | | | | |
| f1 | | | | |
| f2 | 36.88 | 36.88 | 36.88 | 36.88 |
| i | 17.68 | 17.68 | 17.68 | 17.68 |
| h | 45.45 | 45.45 | 45.45 | 45.45 |
| j | | | | |
| Ratio by weight Part A/Part(s)B, C* | 80/20 | 80/20 | 80/20 | 80/20 |

| | | | Comparison | |
|---|---|---|---|---|
| | Ex. 5 | Ex. 6 | Ex. 7 | Ex. 8 |
| Ingredients Part A | | | | |
| a | 15.01 | 18.73 | 18.73 | 15.59 |
| b1 | 45.02 | 56.20 | 56.20 | 46.76 |
| b2 | | 5.99 | 5.99 | |
| b3 | 35.00 | | | 36.35 |
| b4 | | | | |
| c1 | | 9.99 | 9.99 | |
| c2 | 1.25 | | | 1.30 |
| d | 3.09 | 4.10 | 4.10 | 0 |
| e | 0.10 | 0.09 | 0.09 | 0.003 |
| f1 | | 4.90 | 4.90 | |
| g | | 18.73 | | |
| Ingredients Part B (C*) | | | | |
| a | | 9.99* | 9.99 | |
| b1 | | 29.97* | 29.97 | |
| b2 | 0.50 | 29.97* | 29.97 | |
| f1 | | 4.99* | 4.99 | |
| f2 | | | | 36.88 |
| i | 27.89 | 6.99 | 6.99 | 17.68 |
| h | 71.61 | 17.98 | 17.98 | 45.45 |
| j | | 0.10* | 0.10 | |
| Ratio by weight Part A/Part(s)B, C* | 86.3/13.7 | 100/24.97/75.03 | 100/100 | 90/10 |

In Example 6, the composition was made by mixing the three Parts A, B and C (components of Part C are indicated by "*" term).

Examples 1 to 7 are foaming.

Example 8 is non foaming.

3) Sterilization and Crosslinking

Parts A and B were irradiated by gamma, e-beam or X-Ray at various doses included between 10 kGy to 35 kGy.

After sterilisation, each Part was then mixed with the sterilized (or with the non-sterilised such as in Example 6 or 8) corresponding part, according to the ratio mentioned in the Table 1. After curing, the resultant solid or foam elastomers are evaluated and compared with unsterilised elastomers (results recorded in Tables 2 to 5).

4) Tests

As shown by results of Examples 1, 2, 3, 4 and 6, it is possible to irradiate Parts A and B by gamma, e-beam or X-Ray even at high doses (10 kGy to 35 kGy) with no or acceptable slight increase in viscosity. Moreover, the properties of the elastomeric foams are similar to those of the unsterilised foams. The addition of inert silicone oil as diluent to Part B enabled the viscosity and volume of Parts A and B to be balanced.

The Comparative Example 7 demonstrates that the presence in Part B of polysiloxanes having SiH units and of polysiloxanes having SiVinyl units leads to gel or cured pre-polymer after sterilization of Part B. Thus, it is not possible to mix Parts A and B in order to produce the foam. Nevertheless, the Example 5 demonstrates that the presence of 0.5% by weight of a polydimethylsiloxane blocked at each of the chain ends by a $(CH_3)_2ViSiO_{1/2}$ ($M^{Vi}$) unit is acceptable.

TABLE 3-continued

| | | | | | |
|---|---|---|---|---|---|
| Hardness after 1 day at 23° C. (Sh00) | 31 | 33 | 40 | 39 | 42 |
| Manual Kinetic at 23° C. | 3'15" | 2'30" | 2'15" | 2'40" | 3'30" |

| | Example 6 (part P3 was not irradiated) | | |
|---|---|---|---|
| Irradiation technique | None | Gamma | e-beam |
| Irradiation dose on Part A (kGy) | 0 | 0 | 0 |
| Irradiation dose on Part B (kGy) | 0 | 25.0 | 25.2-30.4 |
| Viscosity of Part A (mPa · s) | 5120 | 5120 | 5120 |
| Viscosity of Part B (mPa · s) | <5000 | <5000 | <5000 |
| Density of cured foam (g/cm³) | 0.17 | 0.18 | 0.2 |
| Hardness after 15' at 23° C. (Sh00) | 0 | 0 | 0 |
| Hardness after 1 day at 23° C. (Sh00) | 38 | 37 | 37 |
| Manual Kinetic at 23° C. | 5' | 4'35" | 4'30" |

TABLE 2

| | Example 1 | | | Example 2 | | |
|---|---|---|---|---|---|---|
| Irradiation technique | None | Gamma | Gamma | None | Gamma | Gamma |
| Irradiation dose on Part A (kGy) | 0 | 10.6 | 25.9 | 0 | 25.2 | 35.6 |
| Irradiation dose on Part B (kGy) | 0 | 10.6 | 25.9 | 0 | 25.2 | 35.6 |
| Viscosity of Part A (mPa · s) | 4800 | 6500 | 21570 | 2000 | 4200 | 8200 |
| Viscosity of Part B (mPa · s) | 1750 | 2100 | 2430 | 1700 | 2600 | 2500 |
| Density of cured foam (g/cm³) | 0.2 | 0.23 | 0.21 | 0.2 | 0.27 | 0.23 |
| Hardness after 15' at 23° C. (Sh00) | 15 | 13 | 15 | 19 | 21 | 16 |
| Hardness after 1 day at 23° C. (Sh00) | 30 | 35 | 31 | 31 | 36 | 30 |
| Manual Kinetic at 23° C. | 2'55" | 3'25" | 2'45 | 2'05" | 2'55" | 2'05" |

| | Example 3 | |
|---|---|---|
| Irradiation technique | None | Gamma |
| Irradiation dose on Part A (kGy) | 0 | 25.4 |
| Irradiation dose on Part B (kGy) | 0 | 25.4 |
| Viscosity of Part A (mPa · s) | 1600 | 5200 |
| Viscosity of Part B (mPa · s) | 1700 | 2700 |
| Density of cured foam (g/cm³) | 0.24 | 0.26 |
| Hardness after 15' at 23° C. (Sh00) | 25 | 20 |
| Hardness after 1 day at 23° C. (Sh00) | 41 | 37 |
| Manual Kinetic at 23° C. | 2'55" | 2'55" |

TABLE 3

| | Example 4 | | Example 5 | | |
|---|---|---|---|---|---|
| Irradiation technique | None | X-Ray | None | Gamma | e-beam |
| Irradiation dose on Part A (kGy) | 0 | 26.3 | 0 | 25.1 | 18.1-31.3 |
| Irradiation dose on Part B (kGy) | 0 | 24.4 | 0 | 25.1 | 18.1-31.3 |
| Viscosity of Part A (mPa · s) | 5300 | 17300 | 1700 | 3800 | 3000 |
| Viscosity of Part B (mPa · s) | 1600 | 2700 | 50 | 150 | 40 |
| Density of cured foam (g/cm³) | 0.19 | 0.23 | 0.19 | 0.26 | 0.24 |
| Hardness after 15' at 23° C. (Sh00) | 13 | 13 | 22 | 25 | 25 |

TABLE 4

| | Comparison Example 7 | | | |
|---|---|---|---|---|
| Irradiation technique | None | Gamma | Gamma | e-beam |
| Irradiation dose on Part A (kGy) | 0 | 10.1 | 25.0 | 23.7-23.8 |
| Irradiation dose on Part B (kGy) | 0 | 10.1 | 25.0 | 22.6-23.1 |
| Viscosity of Part A (mPa · s) | 5120 | 6960 | 45200 | 11000 |
| Viscosity of Part B (mPa · s) | 5600 | Gel | Cured | Gel |
| Density of cured foam (g/cm³) | 0.17 | / | / | / |
| Hardness after 15' at 23° C. (Sh00) | 0 | / | / | / |
| Hardness after 1 day at 23° C. (Sh00) | 38 | / | / | / |
| Manual Kinetic at 23° C. | 5' | / | / | / |

As shown by results in Table 5, it is possible to irradiate Parts A and B by gamma or e-beam even at high doses (25 kGy) with no or acceptable slight increase in viscosity.

Moreover, the properties of the elastomers are similar to those of the unsterilised polymers.

Within this boundary level, at H/Vi ratio=5,000 the properties of Part B are minimally changed and function is good.

TABLE 5

| | Example 8 (non-foaming) | | | | |
|---|---|---|---|---|---|
| Irradiation technique | None | Gamma | e-beam | Gamma | e-beam |
| Irradiation dose on Part A (kGy) | 0 | 25.1 | 18.1-31.3 | 0 | 0 |
| Irradiation dose on Part B (kGy) | 0 | 25.1 | 18.1-31.3 | 25. | 18.1-31.3 |
| Viscosity of Part A (mPa · s) | 2400 | 5100 | 3800 | 2400 | 2400 |
| Viscosity of Part B (mPa · s) | 1800 | 2400 | 2500 | 2400 | 2500 |
| Pot-life at 23° C. | 2 h 05 | / | / | 2 h 05 | 2 h 10 |
| Hardness after 1 h at 150° C. (ShA) | 35 | / | / | 34 | 30 |
| Mechanical properties after 1 h at 150° C. T/S (MPa) | 1.8 | / | / | 1.7 | 1.2 |
| E/B (%) | 144 | / | / | 143 | 136 |
| Tr/S (N/mm) | 2.2 | / | / | 2.3 | 2.3 |

EXAMPLE 3

Determination of Tolerated Contaminant Prepolymer (i) in Part B

Compositions were prepared incorporating different amounts of vinyl in Part B and irradiated by gamma or e-beam at 25 kGy.

The composition tested are described in Table 6 below:

TABLE 6

| COMPOSITIONS: Parts by weight | | |
|---|---|---|
| | | Example 9 |
| Components Part A | | |
| Part P1 | a | 15.01 |
| | b1 | 45.02 |
| | b3 | 35.00 |
| | c2 | 1.25 |
| | d | 3.09 |
| | e | 0.10 |
| Components Part B | | |
| Part P2 | b3 | 0.99 |
| | i | 27.75 |
| | h | 71.26 |
| Ratio by weight Part A/Part(s) B | | 86.3/13.7 |

The results are as follows:

| Composition | Effect of irradiation | % wt (i) in Part B | H/Vi ratio |
|---|---|---|---|
| Comparison Example 7 | unacceptable | | <1000 |
| Example 9 | acceptable, slight effect on density (0.18 to 0.28) | (1% of short Vinyl chain) | 10 000-15 000 |
| Example 5 | acceptable | 0.5% of long chain = Example 5 | 80 000-120 000 |

These results show that a low level of prepolymer (i) is acceptable in Part B, which is insufficient to influence the properties of the composition.

We determined a boundary level at which prepolymer (i) is unacceptable in Part B.

At H/Vi ratio=2,000 the properties of Part B are altered but the composition remains functional.

Within this preferred level, at H/Vi=10,000 the properties of Part B are substantially unchanged and function is excellent.

What is claimed is:

1. A curable composition apportioned between at least one Part A and at least one Part B, the composition comprising:
   the at least one Part A comprising one or more alkenyl-group containing polymers including at least one, or at least two, alkenyl group or moiety per molecule,
   the at least one Part B comprising one or more SiH-containing polymers including at least one, or at least two, Si—H unit or moiety per molecule,
   a catalyst for curing by addition of an alkenyl-containing polymer to a SiH-containing polymer, and
   a blowing agent configured to evolve gas as part of or during a curing reaction,
   wherein the SiH-containing polymer is absent from the at least one Part A and the alkenyl-group containing polymer is absent from the at least one Part B or the at least one Part B incorporates a trace amount of the alkenyl-group containing polymer represented as a molar ratio (Si—H unit or moiety)/(alkenyl unit or moiety) of greater than or equal to 2000,
   wherein the at least one Part A and the at least one Part B are configured to be sterilized by irradiation without degradation thereof, and
   wherein the curable composition is configured to form during the curing reaction as a resiliently deformable porous foam configured to transmit negative pressure.

2. A curable composition as claimed in claim 1, wherein the at least one Part A comprises the catalyst.

3. A curable composition as claimed in claim 1, wherein at least one of the at least one Part A or the at least one Part B is sterilized by irradiation.

4. A curable composition as claimed in claim 1, wherein the one or more alkenyl-group containing polymers and the one or more SiH-containing polymers are selected from the group consisting of silicones, including siloxanes and modified siloxanes, polyurethanes (PU) including polyester and polyether urethanes, elastomeric polyether polyesters, polyglycolic acid, polyacetates such as ethyl vinyl acetate, polyacrylate, polyacid derivatives of polysaccharides, such as carboxyalkylcellulose, carboxyalkylchitosan and copolymers thereof, and their hybrids including copolymers, entangled systems and mixtures thereof.

5. A curable composition as claimed in claim 1, wherein:
   the curing reaction by addition of the alkenyl-containing polymer to the SiH-containing polymer further comprises curing between organohydrogensiloxane units and organoalkenylsiloxane units incorporated into polymeric, copolymeric, entangled, and mixed polymer systems, and the alkenyl-containing polymer and the SiH-containing polymer are organosiloxanes.

6. A curable composition as claimed in claim 1, wherein a viscosity ratio of the at least one Part A: the at least one Part B is in the range of 6:1 - 1:8.

7. A curable composition as claimed in claim 1 for medical or non-medical, dental or non-dental use including use as dyes; preservatives; gels; foams; aerosols; pharmaceuticals; adhesives; encapsulants; hair/skin care; cosmetic use; dental use; release coatings; coatings; adhesives and sealants; wound care including wound dressings; skin care including scar reduction; cavity care; medical device encapsulation such as electronic device encapsulation for biomedical applications; mould making; orthopaedics; drug delivery systems including antimicrobial systems; haemostatic and pharmaceutical systems; nutrition including manufacture of foodstuffs; aerospace, marine and submarine applications; ecologically sensitive applications; confined or isolated organisms, or their habitats, or confined or isolated medium or atmosphere such as those having low immunity; sterile, clean or aseptic applications; germination or propagation of living matter such as plants or organisms; including manufacture and repair of equipment, apparatus or components for any of the above and in particular aerospace, submarine, sterile, clean or aseptic, germination or propagation, including use as foams, aerosols, adhesives, release coatings, coatings, adhesives and sealants, wound care in relation to NPWT in a sterile field or environment; and, use as a negative pressure wound therapy wound filling material, adhesive or sealant, wherein the at least one Part A and at least one Part B are adapted to be dispensed in cooperative manner facilitating intimate contact and curing thereof and formation of a porous foam which is capable of transmitting negative pressure, adhering a negative pressure wound therapy drape or which is air-tight.

8. The medical or non-medical use of a composition as claimed in claim 1 selected from the group consisting of use as dyes; preservatives; gels; foams; aerosols; pharmaceuticals; adhesives; encapsulants; hair/skin care; cosmetic use; dental use; release coatings; coatings; adhesives and sealants; wound care; skin care including scar reduction; cavity care; medical device encapsulation such as electronic device encapsulation for biomedical applications; mould making; orthopaedics; drug delivery systems including antimicrobial systems; haemostatic and pharmaceutical systems; nutrition including manufacture of foodstuffs; aerospace, marine and submarine applications; ecologically sensitive applications; confined or isolated organisms, or their habitats, or confined or isolated medium or atmosphere such as those having low immunity; sterile, clean or aseptic applications; germination or propagation of living matter such as plants or organisms; including manufacture and repair of equipment, apparatus or components for any of the above and in particular aerospace, submarine sterile, clean or aseptic, germination or propagation; in wound therapy, including use as foams, aerosols, adhesives, release coatings, coatings, adhesives and sealants, wound care in relation to NPWT in a sterile field or environment, including use as a wound filler or wound packing material or cavity foam dressing, adhesive or sealant; for use as a negative pressure wound therapy wound filling material, wherein the at least one Part A and the at least one Part B are adapted to be dispensed in cooperative manner facilitating intimate contact and curing thereof and formation of a porous foam which is configured to transmit negative pressure, adhering a negative pressure wound therapy drape which is substantially air-tight.

9. A curable composition as claimed in claim 1, wherein the composition is terminally sterile, wherein a sterility level of the composition corresponds to a sterility assurance level (SAL) of equal to or less than $10^{-6}$ such that the theoretical probability of there being a viable microorganism present is equal to or less than $1\times10^{-6}$.

10. A curable composition as claimed in claim 5, wherein the alkenyl-containing polymer and the SiH-containing polymer are polyorganosiloxanes.

11. A curable composition as claimed in claim 1, wherein a viscosity ratio of the at least one Part A: the at least one Part B is in the range of 5:1 -1:5.

12. A curable composition as claimed in claim 1, wherein a viscosity ratio of the at least one Part A: the at least one Part B is 1:1.

13. A curable composition as claimed in claim 1, wherein the at least one Part A and the at least one Part B are sterilized and a viscosity ratio of the at least Part A: the at least Part B is the same before and after sterilization.

14. A curable composition as claimed in claim 1, wherein the blowing agent is selected from the group consisting of methanol, ethanol, n-propanol, isopropanol, n-butanol, 2-butanol, tert-butanol, n-hexanol, n-octanol, benzyl alcohol, 4-butanediol, 1,5-pentanediol, 1,7-heptanediol, silane including at least one silanol group, polysilane including at least one silanol group, water, and combination thereof.

15. A curable composition as claimed in claim 1, wherein the composition further comprises a diluent which is radiation sterilizable.

16. A curable composition as claimed in claim 1, wherein the porous material comprises 70% to 90% free internal volume.

* * * * *